United States Patent
Bonnette et al.

(10) Patent No.: US 8,303,538 B2
(45) Date of Patent: Nov. 6, 2012

(54) RHEOLYTIC THROMBECTOMY CATHETER WITH SELF-INFLATING DISTAL BALLOON

(75) Inventors: Michael J. Bonnette, Minneapolis, MN (US); Eric J. Thor, Arden Hills, MN (US); Debra M. Kozak, Forest Lake, MN (US)

(73) Assignee: Medrad, Inc., Inianola, PA (US)

( * ) Notice: Subject to any disclaimer, the term of this patent is extended or adjusted under 35 U.S.C. 154(b) by 834 days.

(21) Appl. No.: 12/336,750

(22) Filed: Dec. 17, 2008

(65) Prior Publication Data

US 2009/0156983 A1 Jun. 18, 2009

Related U.S. Application Data

(60) Provisional application No. 61/007,852, filed on Dec. 17, 2007.

(51) Int. Cl.
*A61M 29/00* (2006.01)

(52) U.S. Cl. ........... 604/102.01; 604/97.01; 604/102.02; 604/102.03

(58) Field of Classification Search ............... 604/97.01, 604/97.02, 97.03, 98.01, 99.01, 102.01, 102.02, 604/102.03, 103.06
See application file for complete search history.

(56) References Cited

U.S. PATENT DOCUMENTS

| | | | |
|---|---|---|---|
| 3,435,826 A | 4/1969 | Fogarty | |
| 3,695,208 A | 10/1972 | Fixler | |
| 3,752,617 A | 8/1973 | Burlis et al. | |
| 3,833,003 A | 9/1974 | Taricco | |
| 3,930,505 A | 1/1976 | Wallach | |
| 4,168,709 A | 9/1979 | Bentov | |
| 4,224,943 A | 9/1980 | Johnson et al. | |
| 4,248,234 A | 2/1981 | Assenza et al. | |
| 4,290,428 A | 9/1981 | Durand et al. | |
| 4,328,811 A | 5/1982 | Fogarty | |
| 4,385,635 A | 5/1983 | Ruiz | |
| 4,515,592 A | 5/1985 | Frankhouser | |
| 4,535,757 A | 8/1985 | Webster | |
| 4,610,662 A | 9/1986 | Weikl et al. | |
| 4,631,052 A | 12/1986 | Kensey | |

(Continued)

FOREIGN PATENT DOCUMENTS

DE 3421390 C2 7/1986

(Continued)

OTHER PUBLICATIONS

Office Action Issued Mar. 17, 2009 in Corresponding U.S. Appl. No. 11/294,006.

(Continued)

*Primary Examiner* — Bhisma Mehta
(74) *Attorney, Agent, or Firm* — David Schramm

(57) ABSTRACT

The devices of the present disclosure are rheolytic thrombectomy catheters with a self-inflating distal balloon. A self-inflating balloon is located distal to an inflow gap or orifice and distal to a fluid jet emanator, which self-inflating balloon is inflated and expanded by the utilization of internal operating forces consisting of forwardly directed high velocity fluid jet streams and/or entrained thrombus particulate therein. The self-inflating balloon, when inflated, impinges on the wall of the blood vessel to isolate sections of the blood vessel distal and proximal to the inflated balloon in order to prevent flow of thrombus particulate, fluids and the like distal to the self-inflating balloon and to provide a stagnant nonflow region proximal to the self-inflating balloon. The devices of the present disclosure also provide for a uniform spacing of the catheter tube with respect to the thrombus and/or wall of the blood vessel.

10 Claims, 16 Drawing Sheets

U.S. PATENT DOCUMENTS

| | | |
|---|---|---|
| 4,636,346 A | 1/1987 | Gold et al. |
| 4,690,672 A | 9/1987 | Veltrup |
| 4,739,768 A | 4/1988 | Engelson |
| 4,747,405 A | 5/1988 | Leckrone |
| 4,781,186 A | 11/1988 | Simpson et al. |
| 4,782,834 A | 11/1988 | Maguire et al. |
| 4,790,813 A | 12/1988 | Kensey |
| 4,834,710 A | 5/1989 | Fleck |
| 4,842,579 A | 6/1989 | Shiber |
| 4,883,459 A | 11/1989 | Calderon |
| 4,888,146 A | 12/1989 | Dandeneau |
| 4,898,574 A | 2/1990 | Uchiyama et al. |
| 4,898,591 A | 2/1990 | Jang et al. |
| 4,902,276 A | 2/1990 | Zakko |
| 4,913,698 A | 4/1990 | Ito et al. |
| 4,917,667 A | 4/1990 | Jackson |
| 4,950,238 A | 8/1990 | Sullivan |
| 5,011,469 A | 4/1991 | Buckberg et al. |
| 5,015,232 A | 5/1991 | Maglinte |
| 5,042,976 A | 8/1991 | Ishitsu et al. |
| 5,085,549 A | 2/1992 | Londry |
| 5,085,635 A | 2/1992 | Cragg |
| 5,085,649 A | 2/1992 | Flynn |
| 5,086,842 A | 2/1992 | Cholet |
| 5,090,960 A | 2/1992 | Don Michael |
| 5,092,873 A | 3/1992 | Simpson et al. |
| 5,114,399 A | 5/1992 | Kovalcheck |
| 5,135,482 A | 8/1992 | Neracher |
| 5,163,431 A | 11/1992 | Griep |
| 5,171,221 A | 12/1992 | Samson |
| 5,215,614 A | 6/1993 | Wijkamp |
| 5,221,270 A | 6/1993 | Parker |
| 5,222,941 A | 6/1993 | Don Michael |
| 5,234,416 A | 8/1993 | Macaulay et al. |
| 5,242,395 A | 9/1993 | Maglinte |
| 5,250,034 A | 10/1993 | Appling et al. |
| 5,250,059 A | 10/1993 | Andreas et al. |
| 5,254,107 A | 10/1993 | Soltesz |
| 5,259,842 A | 11/1993 | Plechinger et al. |
| 5,267,979 A | 12/1993 | Appling et al. |
| 5,273,526 A | 12/1993 | Dance et al. |
| 5,300,022 A | 4/1994 | Klapper et al. |
| 5,306,249 A | 4/1994 | Don Michael |
| 5,308,342 A | 5/1994 | Sepetka et al. |
| RE34,633 E | 6/1994 | Sos et al. |
| 5,318,518 A | 6/1994 | Plechinger et al. |
| 5,320,599 A | 6/1994 | Griep et al. |
| 5,324,285 A | 6/1994 | Cannon |
| 5,331,679 A | 7/1994 | Hirukawa |
| 5,342,386 A | 8/1994 | Trotta |
| 5,356,388 A | 10/1994 | Sepetka et al. |
| 5,358,485 A | 10/1994 | Vance et al. |
| 5,360,379 A | 11/1994 | Carelli et al. |
| 5,370,609 A | 12/1994 | Drasler et al. |
| 5,372,601 A | 12/1994 | Lary |
| 5,380,307 A | 1/1995 | Chee et al. |
| 5,385,548 A | 1/1995 | Williams et al. |
| 5,399,164 A | 3/1995 | Snoke et al. |
| 5,409,454 A | 4/1995 | Fischell et al. |
| 5,425,723 A | 6/1995 | Wang |
| 5,456,665 A | 10/1995 | Postell et al. |
| 5,456,674 A | 10/1995 | Bos et al. |
| 5,478,330 A | 12/1995 | Imran et al. |
| 5,492,532 A | 2/1996 | Ryan et al. |
| 5,496,267 A | 3/1996 | Drasler et al. |
| 5,496,294 A | 3/1996 | Hergenrother et al. |
| 5,499,973 A | 3/1996 | Saab |
| 5,513,956 A | 5/1996 | Lewis et al. |
| 5,514,092 A | 5/1996 | Forman et al. |
| 5,531,679 A | 7/1996 | Schulman et al. |
| 5,531,685 A | 7/1996 | Hemmer et al. |
| 5,536,242 A | 7/1996 | Willard et al. |
| 5,542,924 A | 8/1996 | Snoke et al. |
| 5,554,121 A | 9/1996 | Ainsworth et al. |
| 5,558,642 A | 9/1996 | Schweich, Jr. et al. |
| 5,571,094 A | 11/1996 | Sirhan |
| 5,599,299 A | 2/1997 | Weaver et al. |
| 5,599,325 A | 2/1997 | Ju et al. |
| 5,609,574 A | 3/1997 | Kaplan et al. |
| 5,624,397 A | 4/1997 | Snoke et al. |
| 5,628,730 A | 5/1997 | Shapland et al. |
| 5,634,897 A | 6/1997 | Dance et al. |
| 5,643,279 A | 7/1997 | Trotta |
| 5,658,263 A | 8/1997 | Dang et al. |
| 5,662,608 A | 9/1997 | Imran et al. |
| 5,662,622 A | 9/1997 | Gore et al. |
| 5,668,702 A | 9/1997 | Nassimi |
| 5,676,659 A | 10/1997 | McGurk |
| 5,681,336 A | 10/1997 | Clement et al. |
| 5,683,345 A | 11/1997 | Waksman et al. |
| 5,687,714 A | 11/1997 | Kolobow et al. |
| 5,702,439 A | 12/1997 | Keith et al. |
| 5,704,926 A | 1/1998 | Sutton |
| 5,713,849 A | 2/1998 | Bosma et al. |
| 5,769,828 A | 6/1998 | Jonkman |
| 5,792,167 A | 8/1998 | Kablik et al. |
| 5,795,322 A | 8/1998 | Boudewijn |
| 5,795,325 A | 8/1998 | Valley et al. |
| 5,817,046 A | 10/1998 | Glickman |
| 5,843,022 A | 12/1998 | Willard et al. |
| 5,900,444 A | 5/1999 | Zamore |
| 5,906,590 A | 5/1999 | Hunjan et al. |
| 5,919,163 A | 7/1999 | Glickman |
| 5,928,181 A | 7/1999 | Coleman et al. |
| 5,929,633 A | 7/1999 | Fischer |
| 5,935,501 A | 8/1999 | Andrews et al. |
| 5,939,320 A | 8/1999 | Littman et al. |
| 5,944,686 A | 8/1999 | Patterson et al. |
| 5,951,513 A | 9/1999 | Miraki |
| 5,957,901 A | 9/1999 | Mottola et al. |
| 5,989,210 A | 11/1999 | Morris et al. |
| 5,989,271 A | 11/1999 | Bonnette |
| 6,001,078 A | 12/1999 | Reekers |
| 6,004,269 A | 12/1999 | Crowley et al. |
| 6,004,339 A | 12/1999 | Wijay |
| 6,022,336 A | 2/2000 | Zadno-Azizi et al. |
| 6,024,729 A | 2/2000 | Dehdashtian et al. |
| 6,027,499 A | 2/2000 | Johnston et al. |
| 6,044,845 A | 4/2000 | Lewis |
| 6,062,623 A | 5/2000 | Lemmen |
| 6,063,069 A | 5/2000 | Cragg et al. |
| 6,068,623 A | 5/2000 | Zadno-Azizi et al. |
| 6,074,374 A | 6/2000 | Fulton |
| 6,096,001 A | 8/2000 | Drasler et al. |
| 6,099,496 A | 8/2000 | Berthiaume et al. |
| 6,106,642 A | 8/2000 | DiCarlo et al. |
| 6,129,697 A | 10/2000 | Drasler et al. |
| 6,129,698 A | 10/2000 | Beck |
| 6,135,977 A | 10/2000 | Drasler et al. |
| 6,165,199 A | 12/2000 | Barbut |
| 6,179,816 B1 | 1/2001 | Mottola et al. |
| RE37,153 E | 5/2001 | Henszey et al. |
| 6,224,570 B1 | 5/2001 | Le et al. |
| 6,241,744 B1 | 6/2001 | Imran et al. |
| 6,258,061 B1 | 7/2001 | Drasler et al. |
| 6,273,880 B1 | 8/2001 | Berg et al. |
| 6,283,950 B1 | 9/2001 | Appling |
| 6,331,176 B1 | 12/2001 | Becker et al. |
| 6,375,635 B1 | 4/2002 | Moutafis et al. |
| 6,395,208 B1 | 5/2002 | Herweck et al. |
| 6,524,300 B2 | 2/2003 | Meglin |
| 6,533,782 B2 | 3/2003 | Howell et al. |
| 6,544,220 B2 | 4/2003 | Shuman et al. |
| 6,592,549 B2 | 7/2003 | Gerdts et al. |
| 6,596,818 B1 | 7/2003 | Zamore |
| 6,652,548 B2 | 11/2003 | Evans et al. |
| 6,656,550 B1 | 12/2003 | Zamore |
| 6,676,637 B1 | 1/2004 | Bonnette et al. |
| 6,749,583 B2 | 6/2004 | Briscoe et al. |
| 6,755,803 B1 | 6/2004 | Le |
| 6,773,452 B2 | 8/2004 | Shaker |
| 6,790,196 B2 | 9/2004 | Kokate et al. |
| 6,834,842 B2 | 12/2004 | Houde |
| 6,875,193 B1 | 4/2005 | Bonnette et al. |
| 6,926,726 B2 | 8/2005 | Drasler et al. |
| 6,929,633 B2 | 8/2005 | Evans et al. |
| 6,939,320 B2 | 9/2005 | Lennox |

| | | |
|---|---|---|
| 6,942,635 B2 | 9/2005 | Rosenblatt et al. |
| 6,945,951 B1 | 9/2005 | Bonnette et al. |
| 7,033,776 B2 | 4/2006 | Toombs |
| 7,131,981 B2 | 11/2006 | Appling et al. |
| 7,163,533 B2 | 1/2007 | Hobbs et al. |
| 7,182,756 B2 | 2/2007 | Saeed et al. |
| 7,220,269 B1 | 5/2007 | Ansel et al. |
| 7,226,433 B2 | 6/2007 | Bonnette et al. |
| 7,314,461 B2 | 1/2008 | Carter et al. |
| 7,369,358 B2 | 5/2008 | Edelman et al. |
| 7,374,560 B2 | 5/2008 | Ressemann et al. |
| 7,396,358 B2 | 7/2008 | Appling et al. |
| 7,399,307 B2 | 7/2008 | Evans et al. |
| 7,422,579 B2 | 9/2008 | Wahr et al. |
| 7,500,982 B2 | 3/2009 | Pepper |
| 7,726,433 B2 | 6/2010 | Satou et al. |
| 8,162,878 B2 | 4/2012 | Bonnette et al. |
| 2001/0051785 A1 | 12/2001 | Bonnette et al. |
| 2001/0051811 A1 | 12/2001 | Bonnette et al. |
| 2001/0053920 A1 | 12/2001 | Shaker |
| 2001/0056257 A1 | 12/2001 | Drasler et al. |
| 2002/0032408 A1 | 3/2002 | Parker et al. |
| 2002/0049423 A1 | 4/2002 | Howell et al. |
| 2002/0068895 A1 | 6/2002 | Beck |
| 2002/0077594 A1 | 6/2002 | Chien et al. |
| 2002/0120226 A1 | 8/2002 | Beck |
| 2002/0188276 A1 | 12/2002 | Evans et al. |
| 2003/0069541 A1 | 4/2003 | Gillis et al. |
| 2003/0088194 A1 | 5/2003 | Bonnette et al. |
| 2003/0139751 A1 | 7/2003 | Evans et al. |
| 2003/0195490 A1 | 10/2003 | Boatman et al. |
| 2004/0006306 A1 | 1/2004 | Evans et al. |
| 2004/0019323 A1 | 1/2004 | Carter et al. |
| 2004/0039306 A1 | 2/2004 | Eberhart et al. |
| 2004/0068248 A1 | 4/2004 | Mooney et al. |
| 2004/0093008 A1 | 5/2004 | Zamore |
| 2004/0193196 A1 | 9/2004 | Appling et al. |
| 2004/0210194 A1 | 10/2004 | Bonnette et al. |
| 2005/0049574 A1 | 3/2005 | Petrick et al. |
| 2005/0059957 A1 | 3/2005 | Campbell et al. |
| 2005/0107738 A1 | 5/2005 | Slater et al. |
| 2006/0016064 A1 | 1/2006 | Boatman et al. |
| 2006/0047239 A1 | 3/2006 | Nita et al. |
| 2006/0054123 A1 | 3/2006 | Stein et al. |
| 2006/0064123 A1 | 3/2006 | Bonnette et al. |
| 2006/0129091 A1 | 6/2006 | Bonnette et al. |
| 2006/0217791 A1 | 9/2006 | Spinka et al. |
| 2007/0010847 A1 | 1/2007 | Pepper |
| 2007/0073233 A1 | 3/2007 | Thor et al. |
| 2007/0282303 A1 | 12/2007 | Nash et al. |
| 2007/0282422 A1 | 12/2007 | Biggs et al. |
| 2008/0033350 A1 | 2/2008 | Wilson et al. |
| 2008/0188830 A1 | 8/2008 | Rosenblatt et al. |
| 2008/0275393 A1 | 11/2008 | Bonnette |
| 2008/0300576 A1 | 12/2008 | Witullo et al. |
| 2008/0306427 A1 | 12/2008 | Bailey |

FOREIGN PATENT DOCUMENTS

| | | |
|---|---|---|
| EP | 0251512 A1 | 1/1988 |
| EP | 0528181 A1 | 2/1993 |
| EP | 1382366 A1 | 1/2004 |
| EP | 1800708 | 12/2008 |
| GB | 1571459 A | 7/1980 |
| WO | 9005493 A1 | 5/1990 |
| WO | 9410917 A1 | 5/1994 |
| WO | 9510232 A1 | 4/1995 |
| WO | WO2007067661 | 6/2007 |

OTHER PUBLICATIONS

Office Action Issued Aug. 31, 2009 in Corresponding U.S. Appl. No. 11/294,006.

Final Rejection Issued Jan. 26, 2010 in Corresponding U.S. Appl. No. 11/294,006.

International Search Report from corresponding International Application PCT/US08/87422, Feb. 12, 2009.

International Search Report from corresponding International Application PCT/US08/87109, Feb. 11, 2009.

Final Rejection from corresponding U.S. Appl. No. 11/294,006, Aug. 6, 2008.

International Search Report from corresponding International Application PCT/US06/46621, Nov. 10, 2008.

Office Action from related U.S. Appl. No. 12/338,376, dated Feb. 1, 2012.

RHEOLYTIC THROMBECTOMY CATHETER WITH SELF-INFLATING DISTAL BALLOON

CROSS REFERENCES TO RELATED APPLICATIONS

This application claims priority from the earlier filed U.S. Provisional Application No. 61/007,852 filed Dec. 17, 2007, and is hereby incorporated into this application by reference as if fully set forth herein.

This patent application is related to patent application Ser. No. 10/455,096 filed on Jun. 5, 2003, entitled "Thrombectomy Catheter Device Having a Self-Sealing Hemostasis Valve," now U.S. Pat. No. 7,226,433.

This patent application is also related to patent application Ser. No. 11/096,592 filed on Apr. 1, 2005, entitled "Rapid Exchange Fluid Jet Thrombectomy Device and Method," now U.S. Pat. No. 7,879,022.

BACKGROUND OF THE DISCLOSURE

1. Field of the Disclosure

The present disclosure sets forth a thrombectomy catheter, but more specifically relates to a rheolytic thrombectomy catheter with a self-inflating distal balloon, alternately referred to herein as the "rheolytic thrombectomy catheter" for purposes of brevity. The terms used herein are not intended to be limited to any particular narrow interpretation unless clearly stated otherwise in this document.

2. Description of the Prior Art

Prior art and its comparison to the devices of the present disclosure are partially set forth herein. Flow cessation of prior art devices to minimize hemolysis and for other reasons has been accomplished via a balloon on a proximally or distally placed guide catheter or by way of proprietary occlusion guidewire technology, such as, but not limited to, the use of balloons on guidewires. Neither of these methods places the occlusive balloon directly and dynamically on the catheter. In general, placing an occlusion device proximally at the guide catheter or the use of a distal protection device will result in the need to upsize the interventional sheath or will result in a substantial increase in the cost of the procedure, or both. The devices of the present disclosure permit the use of the same sized introducer sheath with much less dramatic increase in costs to the physician.

The present disclosure describes a rheolytic thrombectomy catheter utilizing the concept of a continuously formed inflatable and expandable balloon which is continuously formed of the same material as the catheter tube (exhaust tube) and which is automatically inflated by an internal pressurization caused by high velocity fluid jet flows and the like. Such a concept can also be applied to other thrombectomy catheters and systems, such as, but not limited to, all AngioJet® catheters including rapid exchange catheters, over-the-wire catheters, and catheters which are pressurized by a fluid flow source. A self-inflating balloon is located distal to an inflow gap or orifice and distal to a fluid jet emanator. This self-inflating balloon is inflated and expanded by the utilization of internal operating forces consisting of forwardly directed high velocity fluid jet streams and entrained thrombus particulate therein. The self-inflating balloon is aligned within the walls of the blood vessel to isolate sections of the blood vessel distal and proximal to the inflated balloon in order to prevent flow of thrombus particulate, fluids and the like, distal to the self-inflating balloon and to provide a stagnant nonflow region proximal to the self-inflating balloon.

Vessel safety is improved and enhanced by use of the devices of the present disclosure. In previously designed cross flow thrombectomy catheters, vessel damage is primarily inflicted by the inflow orifices. The vessel wall can be sucked in by the negative pressures at the inflow orifices to the point that the internal high velocity jet streams can damage the vessel wall. In fact, merely moving the catheter while the inflow orifices have been sucked onto the vessel wall is a likely mechanism for vessel damage from cross stream catheters. Vessel damage increases with the size of the inflow orifices and with the proximity of the high velocity fluid jet stream origin to the inlet orifice. For the devices of the present disclosure, an inlet gap (inlet orifice) is positionally located away from the vessel wall by the centering action of the self-inflating balloon. Additionally, inflation of the self-inflating balloon ensures centering of the device in the vessel in order that treatment may be provided equally in all circumferential directions. Furthermore, the centering feature enables a greater and more uniform delivery of drugs into tougher mural thrombus. This design enables a more effective and greater removal of tougher and more organized thrombus.

SUMMARY OF THE DISCLOSURE

The general purpose of the devices of the present disclosure are to provide a rheolytic thrombectomy catheter with a self-inflating distal balloon, also referred to as a rheolytic thrombectomy catheter and system sold under the trademark AngioJet®, to elegantly stop and/or impede blood flow in a vessel while simultaneously increasing the efficacy of thrombus removal. Flow cessation optimizes the effectiveness of thrombectomies, embolization containment, and procedures involving drug infusion, as well as minimizing hemolysis. Furthermore, the distal balloon is capable of pulling tough plug material within a conduit, i.e., an embolectomy. Other issues addressed by use of the devices of the present disclosure relate to catheter centering which enables more aggressively sized inflow windows for enhanced performance. Use of devices of the present disclosure also relate to modified embolectomies.

The main structure and feature of the devices described in the present disclosure involve use of a distally located self-inflating balloon integral to and formed from a thin wall section of the exhaust tube of the rheolytic thrombectomy catheter which is inflatingly deployed using the back pressure created by the operation of forwardly and rearwardly directed high velocity fluid jet streams used in a thrombectomy catheter, such as an AngioJet® catheter. More specifically, most of a number of high velocity fluid jet streams are emitted retrograde from an emanator and along an inflow gap to entrain thrombus particles in a blood vessel for exhausting overboard through the lumen of a catheter tube. A lesser number of high velocity fluid jet streams are emitted antegrade from the emanator to inflate a dead ended balloon located distal to the emanator.

The device is a rheolytic thrombectomy catheter and can be used for removal of thrombus in coronary arteries, peripheral arteries or veins, neurological arteries or veins, or arterial venous conduits. By sizing the balloon for the intended vessel, the expanded balloon will be more efficacious in removing more organized clots and could be used just to increase the amount of debris/thrombus removed from a particular vessel length. Use of the device can minimize any distal or proximal embolization and can be used to deliver drugs more effectively in a stagnant field. The distally located balloon can also be used for centering or positioning of the device in a vessel.

Finally, the devices of the present disclosure can be used to minimize hemolysis during operation of the AngioJet® catheter.

The present disclosure describes the addition of a self-inflating distal balloon to any of the AngioJet® catheter models. The self-inflating balloon is distally located with respect to a high velocity fluid jet stream emanator. Although balloons attached to catheters proximally or distally have been suggested in the past, this concept goes one step further by creating a self-inflating balloon out of the distal exhaust tube (Pebax® material or polyurethane, etc.) while using the exhaust pressure of the high velocity fluid jet streams to fill and sustain the self-inflating balloon for purposes of distal protection or occlusion. This arrangement minimizes profile, minimizes the number of components and design complexity, minimizes manufacturing costs, and is very easy to use since the self-inflating balloon is deployed automatically when the rheolytic thrombectomy catheter is activated.

Since AngioJet® catheters remove debris more effectively in a stagnant flow, this device has several applications. Thrombus will in some cases have tough end caps. Thus, if the device is deployed distally and then retracted during activation, the cap material could be withdrawn (potentially into a large introducer sheath). With this in mind, the device should also minimize any distal or proximal embolization. It could also be used to deliver drugs more effectively in a stagnant field. The self-inflating balloon could also be used for centering or positioning the catheter in a vessel to minimize vessel damage caused by unequal cross stream jet positioning. The occlusion of the blood field during activation should also minimize hemolysis. Finally, the self-inflating balloon could also be used to break up clots as it is moved through a blocked vessel, thereby performing a modified embolectomy.

According to one or more embodiments of the present disclosure, there is provided a rheolytic thrombectomy catheter with a self-inflating distal balloon, including a manifold, a catheter tube connected to and extending distally from the manifold, a catheter tube having a proximal section which is connected to and extended distally from the manifold being interrupted distally by an inflow gap to continue as a catheter tube distal section, a high pressure tube extending through portions of the manifold, through the proximal section of the catheter tube, and through a proximal marker band and support ring and extending further across the inflow gap to communicatingly terminate within a fluid jet emanator secured in place in the catheter tube distal section by a distal marker band, a balloon inflation inflow orifice located in the catheter tube distal section, a distally located thin section of the catheter tube distal section comprising a self-inflating balloon located distal to the balloon inflation inflow orifice of the catheter tube distal portion, and a distally located tapered flexible tip located distal to the self-inflating balloon on the catheter tube distal section.

The rheolytic thrombectomy catheter incorporates and exemplifies many of the features and teachings of the present disclosure and includes enhancements of a rheolytic thrombectomy catheter and system sold under the trademark AngioJet®.

One significant aspect and feature of the devices of the present disclosure is a self-inflating distal balloon which is formed from the catheter tube itself.

Another significant aspect and feature of the devices of the present disclosure is a self-inflating distal balloon which is deployed and inflatingly maintained by the back pressure created by the use of rearwardly and forwardly directed high velocity fluid jet streams during the operation of the devices of the present disclosure.

Yet another significant aspect and feature of the devices of the present disclosure is a self-inflating distal balloon, one end of which is fixed and positioned by a marker band with an underlying stabilizing saddle or by another suitable means.

Still another significant aspect and feature of the devices of the present disclosure is a self-inflating distal balloon which is used for the purpose of the cessation of fluid flow in a blood vessel or other conduit.

Another significant aspect and feature of the devices of the present disclosure is a self-inflating distal balloon which is used for the purpose of the cessation of fluid flow in a blood vessel or other conduit in order to maximize the effect of a thrombectomy catheter in terms of debris or tissue removal.

Another significant aspect and feature of the devices of the present disclosure is a self-inflating distal balloon which is used for the purpose of the cessation of fluid flow in a blood vessel or other conduit in order to maximize the effect of a thrombectomy catheter in terms of debris or tissue removal from a distal protection filter wire or balloon.

Yet another significant aspect and feature of the devices of the present disclosure is a self-inflating distal balloon used for the purpose of centering the catheter.

Still another significant aspect and feature of the devices of the present disclosure is a self-inflating distal balloon used for the purpose of a modified embolectomy.

Another significant aspect and feature of the devices of the present disclosure is the use of devices for the purpose of infusing drugs into a thrombus adhering to a vessel wall or for treatment of a vessel wall.

Still another significant aspect and feature of the devices of the present disclosure is a distal balloon which is inflated primarily by forwardly facing jets.

Yet another significant aspect and feature of the devices of the present disclosure is a self-inflating distal balloon which inflation is assisted by fluid entrainment inflow produced by forwardly facing high velocity fluid jet streams passing a balloon inflation inflow orifice.

Still another significant aspect and feature of the devices of the present disclosure is the influence of rearwardly directed and forwardly directed jets where a distal balloon is inflated by high velocity fluid jet streams emanating from the forwardly facing jets and where the high velocity fluid jet streams emanating from the rearwardly facing jets provide for proximally directed entrainment of particulate via an inflow gap or orifice to remove such particulate proximally.

Another significant aspect and feature of the devices of the present disclosure is a self-inflating distal balloon having a diameter which could range from 2-20 mm.

Yet another significant aspect and feature of the devices of the present disclosure is a self-inflating distal balloon which could range from 2-200 mm in length.

Still another significant aspect and feature of the devices of the present disclosure is a self-inflating distal balloon which may be compliant, semi-compliant, or noncompliant in nature.

Still another significant aspect and feature of the devices of the present disclosure is a self-inflating distal balloon having an internal operating pressure up to 20 ATM.

Having thus briefly described one or more embodiments of the devices of the present disclosure and having mentioned some significant aspects and features of the devices of the present disclosure, it is the principal object of the present disclosure to provide a rheolytic thrombectomy catheter for use in procedures involving the removal of thrombus.

BRIEF DESCRIPTION OF THE DRAWINGS

Other objects of the devices of the present disclosure and many of the attendant advantages of same will be readily appreciated as they become better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
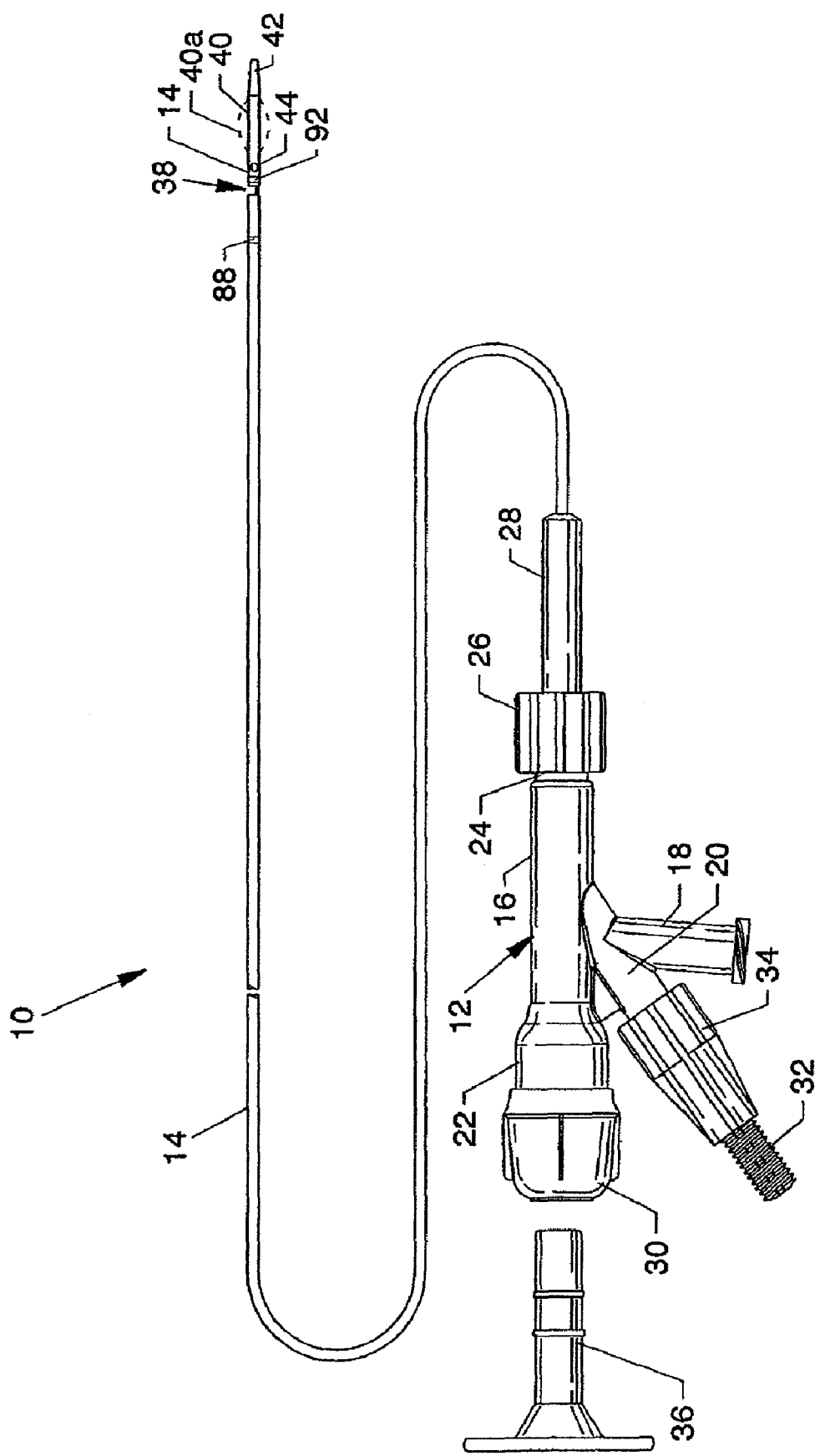
FIG. 1 is a plan view of the visible components of a rheolytic thrombectomy catheter.

FIG. 1 is a plan view of the visible components of rheolytic thrombectomy catheter 10. The device includes a one-piece manifold 12 having multiple structures extending therefrom or attached thereto, and also includes a flexible catheter tube 14, preferably constructed of one or more sections of Pebax® material, and other components associated therewith as described herein. The visible portion of the one-piece manifold 12 includes a central tubular body 16 (e.g., central elongated tubular body), a threaded exhaust branch 18 and a high pressure connection branch 20 extending angularly from central tubular body 16, a partially shown cavity body 22 extending proximally from central tubular body 16 and a threaded connection port 24 extending distally from central tubular body 16. The proximal end of catheter tube 14 is secured to manifold 12 by the use of a Luer fitting 26 accommodated by threaded connection port 24. The proximal end of catheter tube 14 extends through a strain relief tube 28 and through Luer fitting 26 to communicate with manifold 12. Also shown is a hemostasis nut 30 in alignment with and threadingly engaged with the proximal region of cavity body 22. A threaded high pressure connection port 32 is secured to high pressure connection branch 20 by a Luer connector 34. An introducer 36 is also shown.

Figure 2:
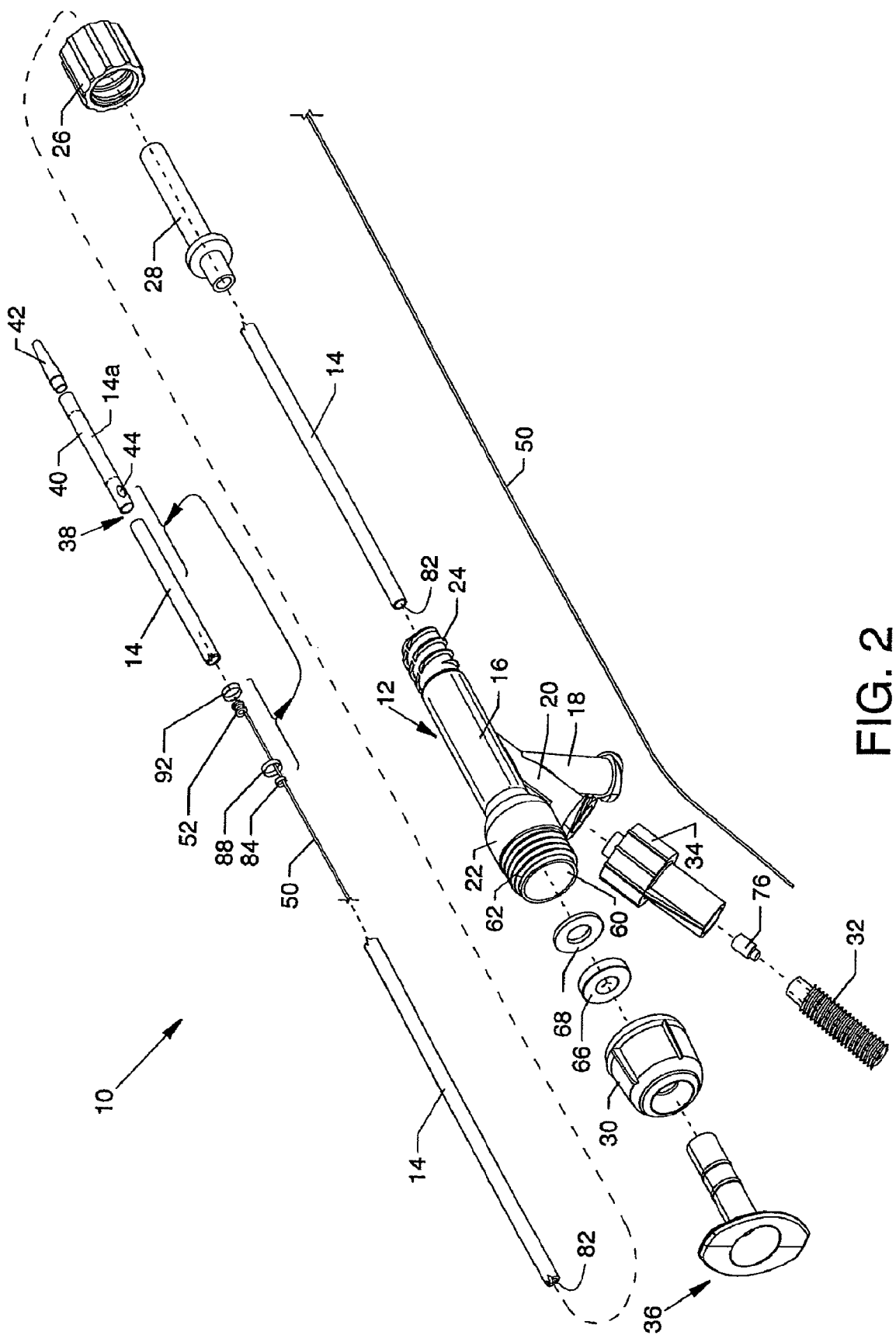
FIG. 2 is an isometric exploded and segmented view of the rheolytic thrombectomy catheter.
Figure 4:
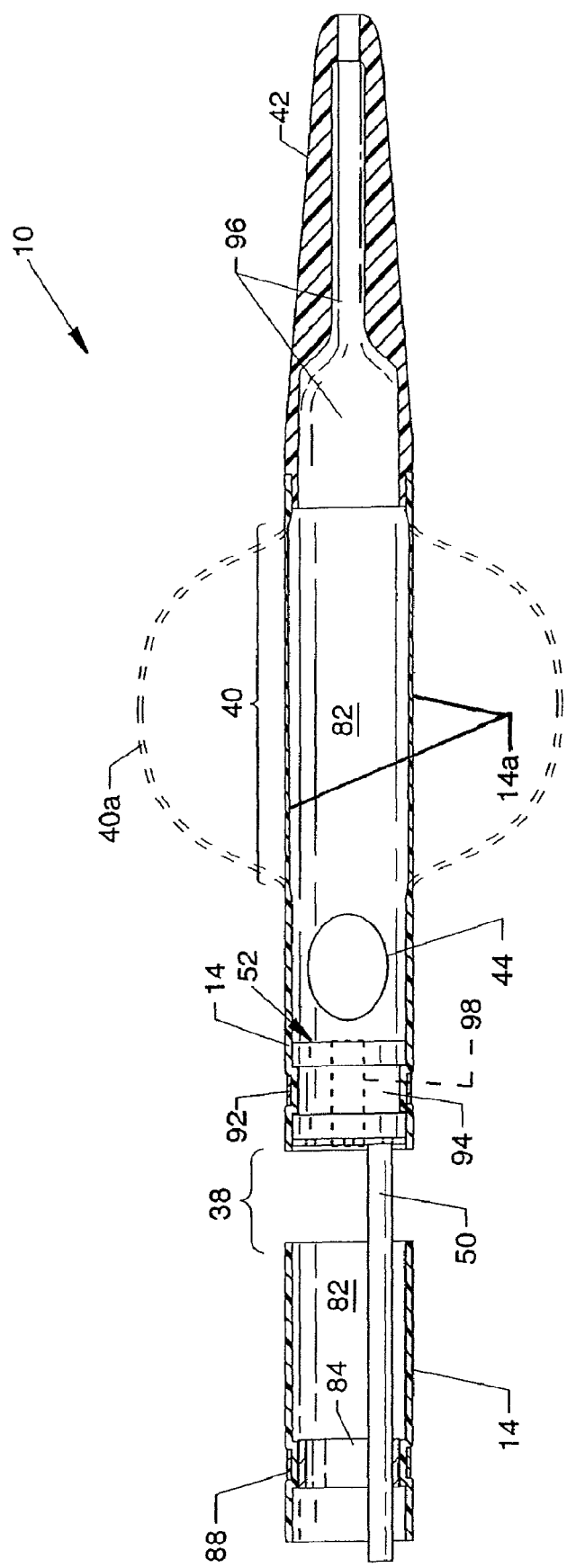
FIG. 4 is a partial cross section of the catheter distal section and a portion of the catheter proximal section.
Figure 5:
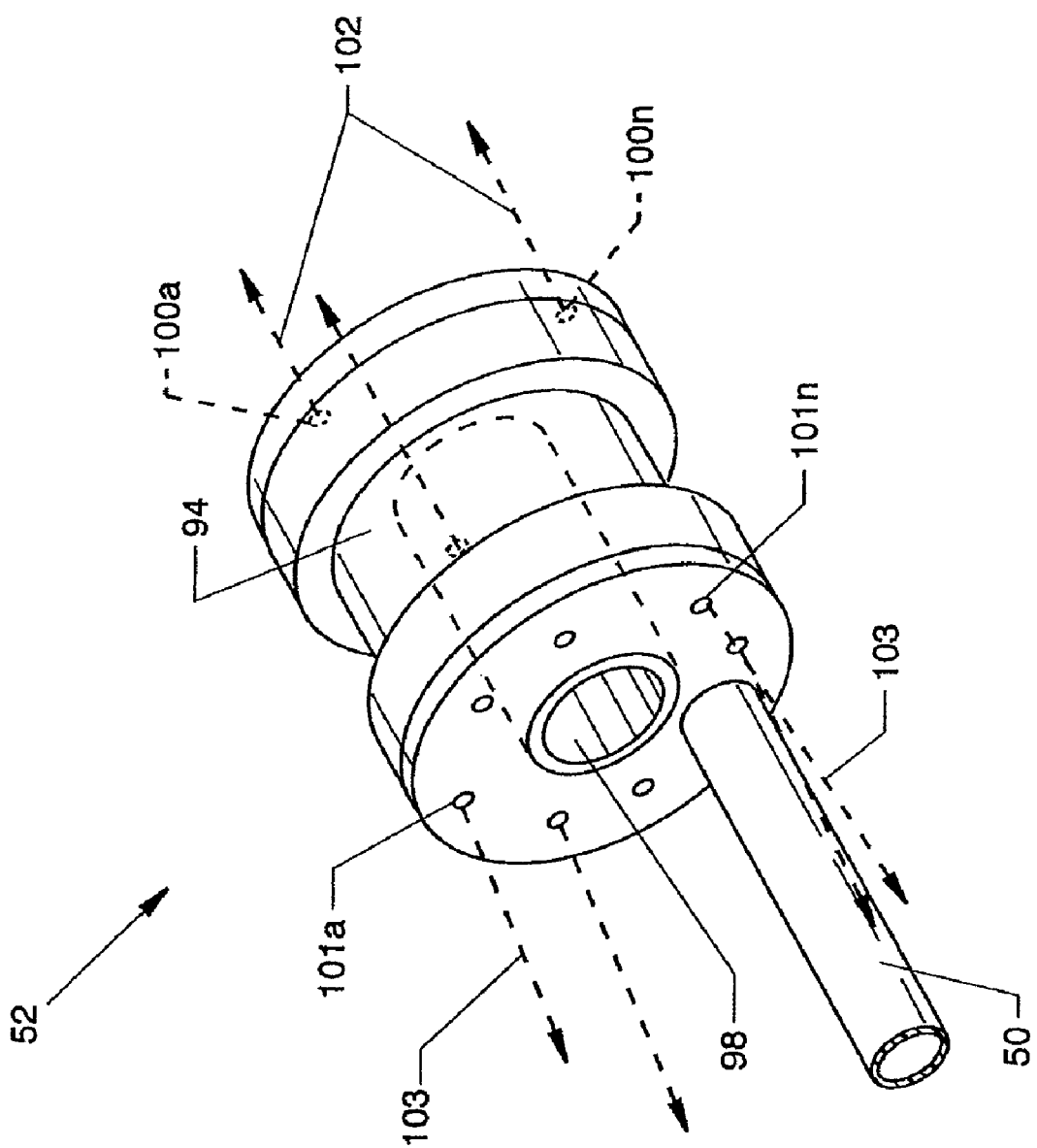
FIG. 5 is an isometric view of the fluid jet emanator shown connected to and in communication with a high pressure tube.

Catheter tube 14 extends distally and is interrupted by an annular inflow gap 38 between the proximal and distal sections of catheter tube 14. The proximal section of catheter tube 14 is that section which is proximal to inflow gap 38. The distal section of catheter tube 14, i.e., that part of which is distal to inflow gap 38, includes a self-inflating balloon 40 (shown as an inflated balloon 40a by dashed lines) which is integral to the distal section of catheter tube 14. A tapered flexible tip 42 extends distally from the distal section of catheter tube 14 and is secured thereto. A fluid jet emanator 52, not shown in FIG. 1 but shown in FIGS. 2, 4 and 5, is located distal to inflow gap 38 inside of the distal section of catheter tube 14. A balloon inflation inflow orifice 44 is located at and extends through the proximal portion of the distal section of catheter tube 14. Balloon inflation inflow orifice 44 in this embodiment, as well as in the later described alternative embodiments, may have more than one balloon inflation inflow orifice. The proximal section of catheter tube 14 functions as an exhaust tube for the evacuation of macerated effluence, thrombus, fluids or other debris from the site of a thrombus or lesion. Preferably, catheter tube 14 includes a hydrophilic coating to enhance deliverability along the vasculature or other structure. Catheter tube 14 is made from a flexible plastic material such as Pebax® or another suitable flexible material.

Figure 3:
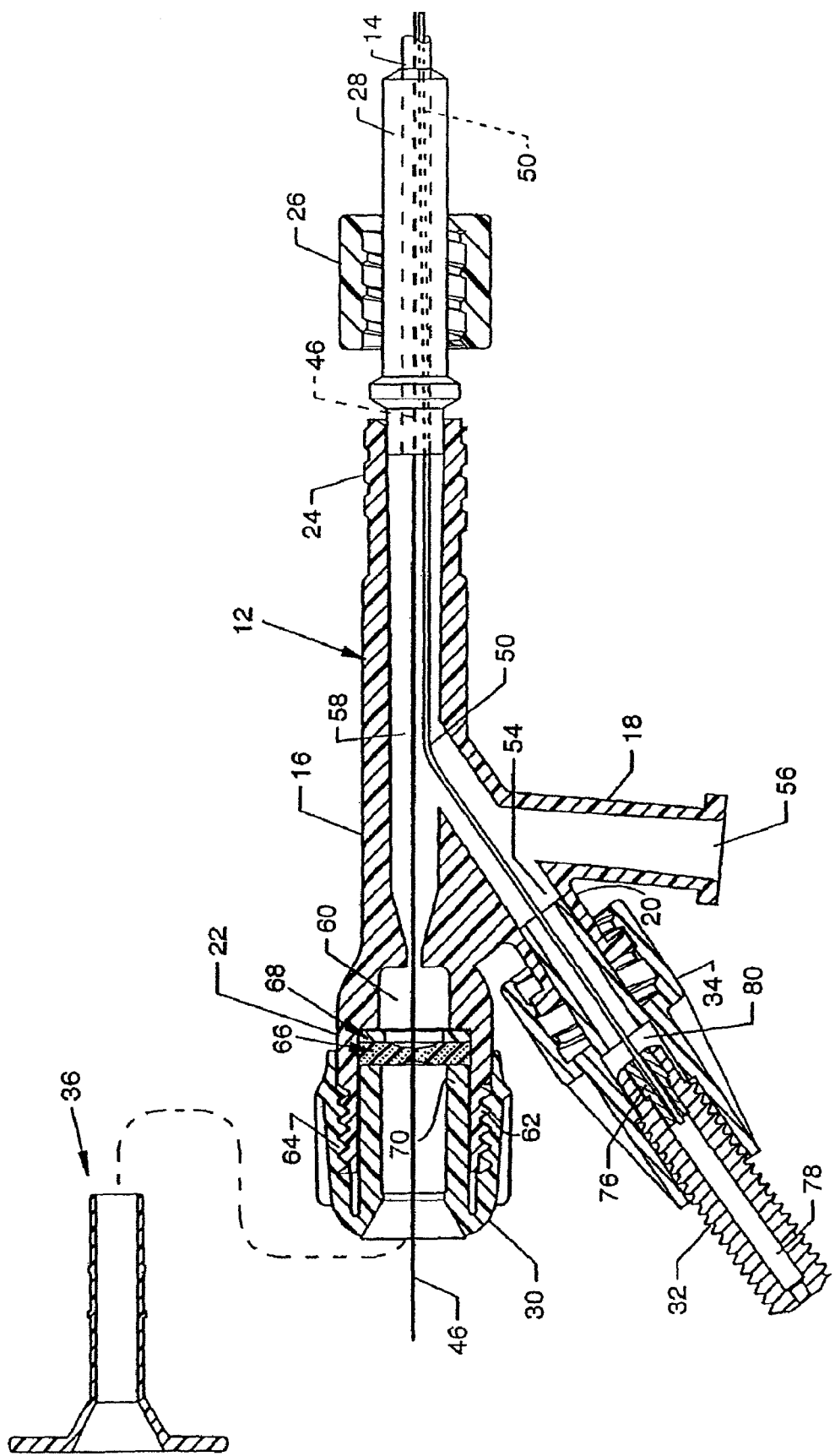
FIG. 3 is an assembled view, in partial cross section, of the components of the manifold and closely associated components and features thereof, including a guidewire.

FIG. 2 is an isometric exploded and segmented view of rheolytic thrombectomy catheter 10, and FIG. 3 is an assembled view, in partial cross section, of the components of manifold 12 and closely associated components and features thereof, including a guidewire 46 such as is incorporated in the use of devices of the present disclosure.

A collection of assembled components, including a high pressure tube 50 and a fluid jet emanator 52, deliver a high pressure saline or other suitable fluid to the distal section of catheter tube 14 for creation of high velocity fluid jet streams which are directed both proximally and distally from fluid jet emanator 52, as later described in detail. High pressure tube 50, preferably of flexible stainless steel or other suitable material, originates within closely associated features or components attached to manifold 12 and passes through and is generally distal to strain relief tube 28 and extends along a greater portion of and within lumen 82 of catheter tube 14 to terminate at fluid jet emanator 52. The distal end of high pressure tube 50, including fluid jet emanator 52, is also shown in greater detail in FIGS. 4 and 5.

With reference to FIGS. 2 and 3, manifold 12 has connected and communicating passageways and cavities (FIG. 3) including a high pressure connection branch passageway 54, an exhaust branch passageway 56, a tapered central passageway 58 extending from and through threaded connection port 24 and through central tubular body 16 to and communicating with a multiple radius cavity 60, which preferably is cylindrical and located central to cavity body 22. External threads 62 are located about the proximal portion of cavity body 22 at the proximal region of manifold 12 for accommodating of internal threads 64 of hemostasis nut 30.

Beneficial to the devices of the present disclosure is the use of a flexible self-sealing hemostasis valve 66, and the use of a washer 68 which is located distal to self-sealing hemostasis valve 66, the shapes and functions of which are described in the referenced U.S. Pat. No. 7,226,433. Self-sealing hemostasis valve 66 and washer 68 are aligned in and housed within the greater radius portion of the multiple radius cavity 60 of cavity body 22. Hemostasis nut 30 includes a centrally located cylindrical boss 70. Washer 68 and self-sealing hemostasis valve 66 are captured within the greater radius portion of multiple radius cavity 60 by threaded engagement of hemostasis nut 30 to threads 62 at the proximal end of manifold 12. Cylindrical boss 70 is brought to bear against the collective self-sealing hemostasis valve 66 and washer 68 bringing pressure to bear, as required, against self-sealing hemostasis valve 66, which pressure culminates in a forcible sealing of self-sealing hemostasis valve 66 about guidewire 46. Although one method of sealing against a guidewire is briefly shown and described, it is appreciated that other methods can be incorporated into this and other forms of devices of the present disclosure such as those methods referenced in U.S. Pat. No. 7,226,433.

Also shown is a ferrule 76 which is aligned within a passageway 78 of threaded high pressure connection port 32, the combination of which is partially aligned within an interior passageway 80 of Luer connector 34. The proximal end of flexible high pressure tube 50 (e.g., elongated flexible high pressure tube), shown in segmented form in FIG. 2, can be utilized for the delivery of high pressure ablation liquids or for the delivery of drugs or other liquids and is suitably secured in a central passageway of ferrule 76 to communicate with interior passageway 78 of threaded high pressure connection port 32, as shown in FIG. 3. The threaded high pressure connection port 32 serving as a fluid source for the flexible high pressure tube 50, wherein the port 32 is connected with a saline reservoir or injection system. The proximal end of high pressure tube 50 also extends through the high pressure connection branch passageway 54, through part of tapered central passageway 58, through strain relief tube 28 and Luer fitting 26, and through a lumen 82 of catheter tube 14.

As shown in FIG. 4, high pressure tube 50 extends through support ring 84 and is suitably connected thereto to provide an anchoring and alignment structure for high pressure tube 50 in order to affix the distal portion of high pressure tube 50 at the proximal end of the distal section of catheter tube 14. In addition, high pressure tube 50 also extends through radiopaque marker band 88. The concentrically aligned radiopaque marker band 88 and support ring 84 are shown forcibly contacting the full wall thickness of catheter tube 14 adjacent the distal end of the proximal section of catheter tube 14. High pressure tube 50 preferably is attached to support ring 84, such as by welding or other suitable means, where support ring 84 functions as a support for catheter tube 14 in the region beneath radiopaque marker band 88. A short distal section of high pressure tube 50 extends across inflow gap 38 and terminates within an internal annular manifold (not shown) of fluid jet emanator 52 and is suitably attached thereto where fluid jet emanator 52 communicates with the lumen of high pressure tube 50, such as in the closely related fluid jet emanator described in the previously referenced patent application Ser. No. 11/096,592 or other applications or patents assigned to the assignee. Fluid jet emanator 52, also shown in FIG. 5 as an isometric view, includes an annular groove 94 which is in coordinated use with a radiopaque marker band 92 on catheter tube 14 to secure fluid jet emanator 52 within the proximal end of the distal section of catheter tube 14 (see FIG. 4). Other designs for fluid jet emanator, 52 such as those disclosed in U.S. Pat. Nos. 5,370,609 and 6,676,637, both of which are incorporated herein by reference, can also be utilized with the devices of the present disclosure, along with other designs and securitization methods described in the literature by the assignee of the present disclosure. The distally located radiopaque marker band 92 is forcibly applied around the proximal end of the distal section of catheter tube 14 to cause a frictional annular engagement with all or part of an annular groove 94 of the fluid jet emanator 52. Such frictional engagement is sufficient to place the outer radial surface of both radiopaque marker bands 92 and 88 in a position lesser than the general and greater outer radial surface of catheter tube 14, thereby providing, in part, a catheter tube 14 having no elements protruding beyond the general outer radial surface thereof for an unimpeded and smooth distal or proximal transition of catheter tube 14 within a vein, artery or the like. A passageway 98 (FIG. 5) is shown central to fluid jet emanator 52 to accommodate the passage of a guidewire 46 (shown in FIG. 3). Tapered flexible tip 42 is shown in FIG. 4 suitably secured to the distal end of the distal section of catheter tube 14. Tapered flexible tip 42 includes a multiple radius inner passageway 96 for the accommodation of a guidewire 46. In FIG. 2, radiopaque marker band 88 is shown displaced a short distance distal to support ring 84 and fluid jet emanator 52 is shown displaced proximally a short distance from radiopaque marker band 92 for the purpose of clarity, but are shown in frictional engagement in their actual positions along and with respect to the distal section of catheter tube 14 in FIG. 4.

The relationships of radiopaque marker bands 88 and 92, support ring 84, and fluid jet emanator 52, respectively, to each other and to catheter tube 14, are shown best in FIG. 4. In FIG. 4, self-inflating balloon 40 is shown contiguous with the distal section of catheter tube 14, wherein self-inflating balloon 40 has a reduced wall thickness 14a when compared to the general wall thickness of catheter tube 14. The reduced wall thickness 14a of self-inflating balloon 40 is of a suitable thickness in order to allow the inflation of self-inflating balloon 40 to thereby expand, meet and align against the wall of the vasculature or against the thrombus, whereby a thrombectomy procedure, drug delivery procedure or other procedure can take place. For the purpose of demonstration and illustration, self-inflating balloon 40 can range in length from 2 mm to 200 mm. When self-inflating balloon 40 is in the inflated state, as represented by inflated balloon 40a, the central diameter of self-inflating balloon 40 can range from 2 mm to 20 mm. Inflated balloon 40a can be expanded, as desired, with an internal pressure up to 20 ATM. Expansion of self-inflating balloon 40 is shown by dashed lines 40a. Alternatively, reduced wall thickness 14a of self-inflating balloon 40 can be formed from other materials, as known in the art, and then bonded or extruded to catheter tube 14 to maintain a continuous structure throughout the length of catheter tube 14 (e.g., in the examples described herein and shown in the drawings the elongate flexible catheter tube 14 is substantially continuous from the proximal section through the elongated distal section containing the self-inflating balloon 40 therein).

Structure is provided to nurture and aid the introduction and passage of the distal portion of catheter tube 14 through blood vessels, arteries and the like to the sites of thrombotic deposits or lesions. Tapered flexible tip 42, as opposed to a rounded and nontapered flexible tip, can part and more easily penetrate thrombotic deposits or lesions during its insertional travel in a distal direction instead of advancing or pushing such thrombotic deposits or lesions distally. The decreasing diameter in a distal direction of tapered flexible tip 42 also allows for an increased flexibility in negotiating and passing through tortuous paths.

Exhaust tube support ring 84 in combination with radiopaque marker band 88 and fluid jet emanator 52 within and about the proximal and distal sections of catheter tube 14, respectively, are examples of structures offering support or reinforcement along catheter tube 14. Such a support ring 84, marker bands 88 and 92, and the external structure of fluid jet emanator 52 provide for the use of a thinner wall thickness for catheter tube 14 and allow for a larger and more effective and efficiently sized lumen 82 of catheter tube 14, as well as contributing to a reduced sized outer diameter. Such support rings and external structure of fluid jet emanator 52 also contribute to supportively maintain the diameter and overall shape of catheter tube 14 when catheter tube 14 is pushed or advanced along a vein or vessel, as well as aiding in torsional support.

FIG. 5 is an isometric view of fluid jet emanator 52 shown connected to and in communication with high pressure tube 50. Fluid jet emanator 52 includes the previously described annular groove 94 and passageway 98 as well as a plurality of forwardly (distally) directed orifices 100a-100n and a plurality of rearwardly (proximally) directed orifices 101a-101n in parallel to the longitudinal axis of fluid jet emanator 52. The distal portion of high pressure tube 50 delivers a high pressure saline or other suitable fluid to fluid jet emanator 52 for the creation and distribution of high velocity fluid jet streams 102 of saline or other suitable fluids which are directed distally from the orifices 100a-100n of fluid jet emanator 52 to perform functions as described herein. Fluid jet emanator 52 also creates and distributes high velocity fluid jet streams 103 of saline or other suitable fluids which are directed proximally from orifices 101a-101n to perform functions as described herein. Although the use of the particular style of fluid jet emanator 52 is shown, other fluid jet emanators having other configurations emanating high velocity fluid jet streams 102 and 103 can also be used in lieu of fluid jet emanator 52 and the use of other fluid jet emanators shall not be considered to be limiting to the scope of the present disclosure.

Mode of Operation

Generally, a normal guidewire is deployed in a vessel requiring treatment or, in the alternative, a filter guidewire or balloon occlusion guidewire could also be used. Distally located components of the rheolytic thrombectomy catheter 10 consisting mainly of catheter tube 14, high pressure tube 50, fluid jet emanator 52, the distal section of catheter tube 14, and uninflated balloon 40 and other components directly associated therewith, are advanced over and/or along a guidewire in the vasculature for the purpose of debris/thrombus removal, drug infusion, or other procedures and maneuvered into the appropriate position for treatment. A guide catheter or sheath can be incorporated as necessary to offer assistance in placing catheter tube 14 of the rheolytic thrombectomy catheter 10 within the desired location of the vasculature. Rheolytic thrombectomy catheter 10 is then activated, wherein self-inflating balloon 40 is automatically and expandingly deployed reforming as an expanded balloon 40a, and then thrombus, debris and the like are removed or drugs can be infused by a desired procedure. Self-inflating balloon 40 can be alternately pressurized and depressurized, whereby rheolytic thrombectomy catheter 10 may be moved proximally or distally during the procedure to maximize the effect of the system. When the procedure is complete, self-inflating balloon 40 is generally deflated sufficiently under normal arterial pressure to be removed safely, or deflation can be aided with a manual syringe attached to an effluent line, or deflation can be aided by means of a roller pump. Further interventions can be executed as normal over the remaining guidewire or guidewire device.

Figure 6:
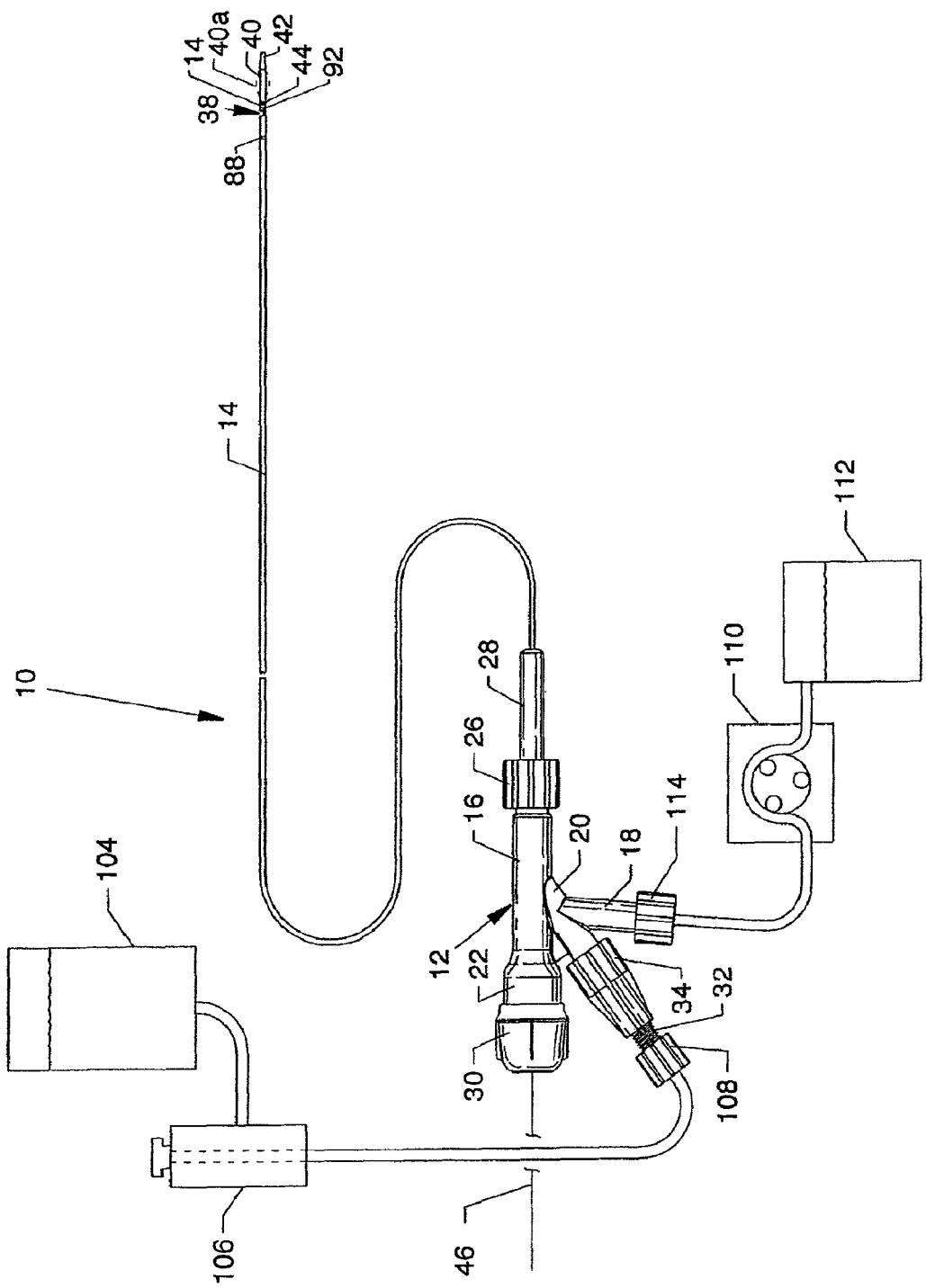
FIG. 6 illustrates the device as connected to ancillary devices for use.
Figure 7:
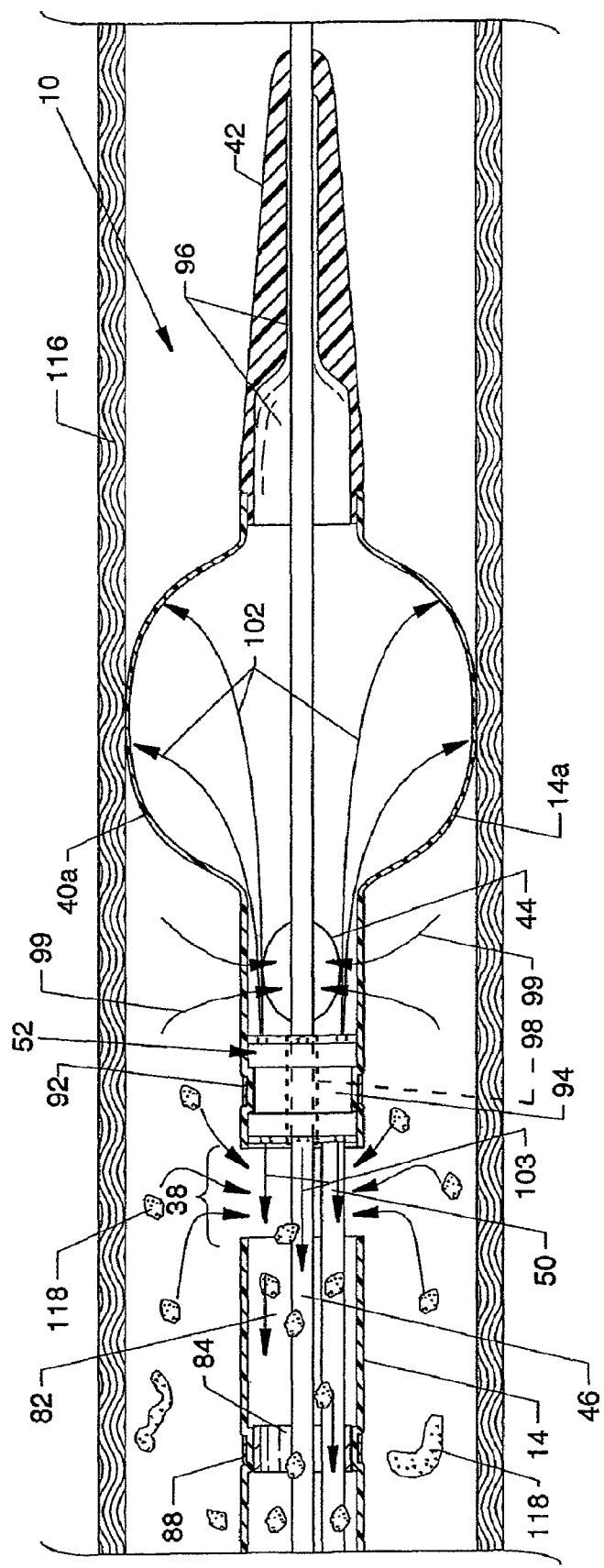
FIG. 7 is a side view, in partial cross section, of the rheolytic thrombectomy catheter in the performance of the method and use thereof.

More specifically, FIGS. 6 and 7 illustrate the mode of operation, where FIG. 6 illustrates rheolytic thrombectomy catheter 10 connected to ancillary devices, and FIG. 7 illustrates the distal portion of rheolytic thrombectomy catheter 10 in the performance of the method and use of the devices of the present disclosure. The mode of operation is best understood by referring to FIGS. 6 and 7 along with the previously described figures.

In FIGS. 5, 6 and 7, rheolytic thrombectomy catheter 10 is shown engaged over and about a guidewire 46, wherein guidewire 46 (described herein from the distal to proximal direction) slidably passes through passageway 96 of tapered flexible tip 42, into and through lumen 82 of the distal section of catheter tube 14, past balloon inflation inflow orifice 44, followed by transiting passageway 98 of fluid jet emanator 52, past inflow gap 38, followed by transiting the distal end of lumen 82 at the proximal section of catheter tube 14, strain relief tube 28, tapered central passageway 58 (FIG. 3), slidably within and in sealed engagement with hemostasis valve 66 (FIG. 3) and through hemostasis nut 30. A high pressure fluid source 104 and a high pressure fluid pump 106 are connected to manifold 12 via threaded high pressure connection port 32 and connector 108. The fluid source may consist of saline, one or more drugs for attacking the thrombus, or a mixture of saline and one or more drugs. An exhaust regulator 110, such as a roller pump or other suitable device, and collection chamber 112 are connected to threaded exhaust branch 18 by a connector 114, as shown.

FIG. 7 is a side view, in partial cross section, of rheolytic thrombectomy catheter 10 in the performance of the method and use thereof with particular attention given to the distal section of catheter tube 14, flexible tapered tip 42, balloon inflation inflow orifice 44, inflated balloon 40a interposed between flexible tapered tip 42 and the balloon inflow orifice 44, fluid jet emanator 52, inflow gap 38, and other closely associated components positioned in a blood vessel 116 containing thrombotic particulate and/or debris 118.

The distal portion of high pressure tube 50 delivers a high pressure saline or other suitable fluid to fluid jet emanator 52 to produce and distribute high velocity fluid jet streams 102 of saline or other suitable fluids which are directed distally from the orifices 100a-100n (FIG. 5) of fluid jet emanator 52 within and along the distal section of catheter tube 14 in close proximity to balloon inflation inflow orifice 44 and thence within the confines of self-inflating balloon 40 resulting in inflated balloon 40a for the purposes of, but not limited to, impeding fluid flow within blood vessel 116 to effect a stagnate flow in the thrombectomy region, to provide centering of the distal section of catheter tube 14, and to accomplish thrombectomy functions as described herein. The high pressure saline, or other suitable fluid, is delivered by high pressure tube 50 to fluid jet emanator 52 to produce and distribute high velocity fluid jet streams 103 of saline or other suitable fluids which are directed proximally from the orifices 101a-101n (FIG. 5) of fluid jet emanator 52, and thence to transit and cross inflow gap 38, and finally into the distal end of the proximal section of catheter tube 14 where other functions as described herein are performed.

Self-inflating balloon 40 is automatically and expandingly deployed to reform as an inflated balloon 40a primarily by the pressure of pressurized distally directed high velocity fluid jet streams 102 emanating from the jet orifices 100a-100n of fluid jet emanator 52. Fluid entrainment inflow 99, shown by the directed arrows in FIG. 7 of the first embodiment, as well as in the later described alternative embodiments, assists in the inflation of the self-inflating balloon. Pressurized inflation of inflated balloon 40a or maintaining a state of inflation is also assisted by utilizing back pressure along the length of catheter tube 14. An operational advantage is the utilization of the exhaust outflow and internal pressure which is created by high velocity fluid jet stream(s) 103 in combination with the restriction of the outflow, such as influenced by exhaust regulator 110, to cause automatic expansion of balloon 40 which forcibly impinges and seals against the inner walls of blood vessel 116. The reduced thickness of the material comprising balloon 40 allows balloon 40 to expand sufficiently to become an inflated balloon 40a restricted by impingement with the wall of blood vessel 116. Inflation pressure and fluid flows can be influenced by controlling of the input pressure fluid at high pressure fluid pump 106 and/or by controlling of the exhaust rate at exhaust regulator 110. Other fluid jet emanators of appropriate size and/or configuration can be incorporated in lieu of fluid jet emanator 52 within the proximal end of the distal section of catheter tube 14 to emanate or emit one or more high velocity fluid jet streams 102 distally and to emanate or emit one or more high velocity fluid jet streams 103 proximally along or near the longitudinal axis of catheter tube 14.

Inflation of balloon 40 to form inflated balloon 40a positions the peripheral circumference of inflated balloon 40 against the wall of blood vessel 116 in order to effect a fluid flow reduction or cessation within blood vessel 116. Inflated balloon 40a, i.e., balloon 40, can be compliant, semi-compliant, or noncompliant according to the procedure performed. Inflated balloon 40a provides uniform centering and positioning of the distal section of catheter tube 14 within blood vessel 116, thereby providing substantially equal spacing between the wall of blood vessel 116 and inflow gap 38 for uniform access and clearance thereto and thereabout. Inflated balloon 40a also provides a spacing between blood vessel 116 and balloon inflation inflow orifice 44 in order to provide access and clearance to and about balloon inflation inflow orifice 44.

High velocity fluid jet streams 103 provide a low pressure region at inflow gap 38 to ingest and entrain thrombotic particulate and/or debris 118 therethrough to impinge on, provide drag forces on, and break up or macerate thrombotic particulate and/or debris 118. Then, by entrainment, these jet streams urge and carry along one or more particles of thrombotic particulate and/or debris 118 or lesion particulate along lumen 82 of catheter tube 14. The entrainment of thrombotic particulate and/or debris 118 through inflow gap 38 is based on entrainment by high velocity fluid jet streams 103. The outflow of fluid and thrombus is driven proximally through catheter tube 14 by an internal pressure which is produced by high velocity fluid jet streams 103 and the fluid entrained through inflow gap 38. Cessation of fluid flow in a blood vessel or other conduit maximizes the effect of rheolytic thrombectomy catheter 10 in terms of debris or tissue removal. Use of the devices of the present disclosure can also provide for the performance of a modified embolectomy by breaking up clots as inflated balloon 40a is moved through a blocked vessel or can be used to minimize any distal or proximal embolization.

Figure 8:
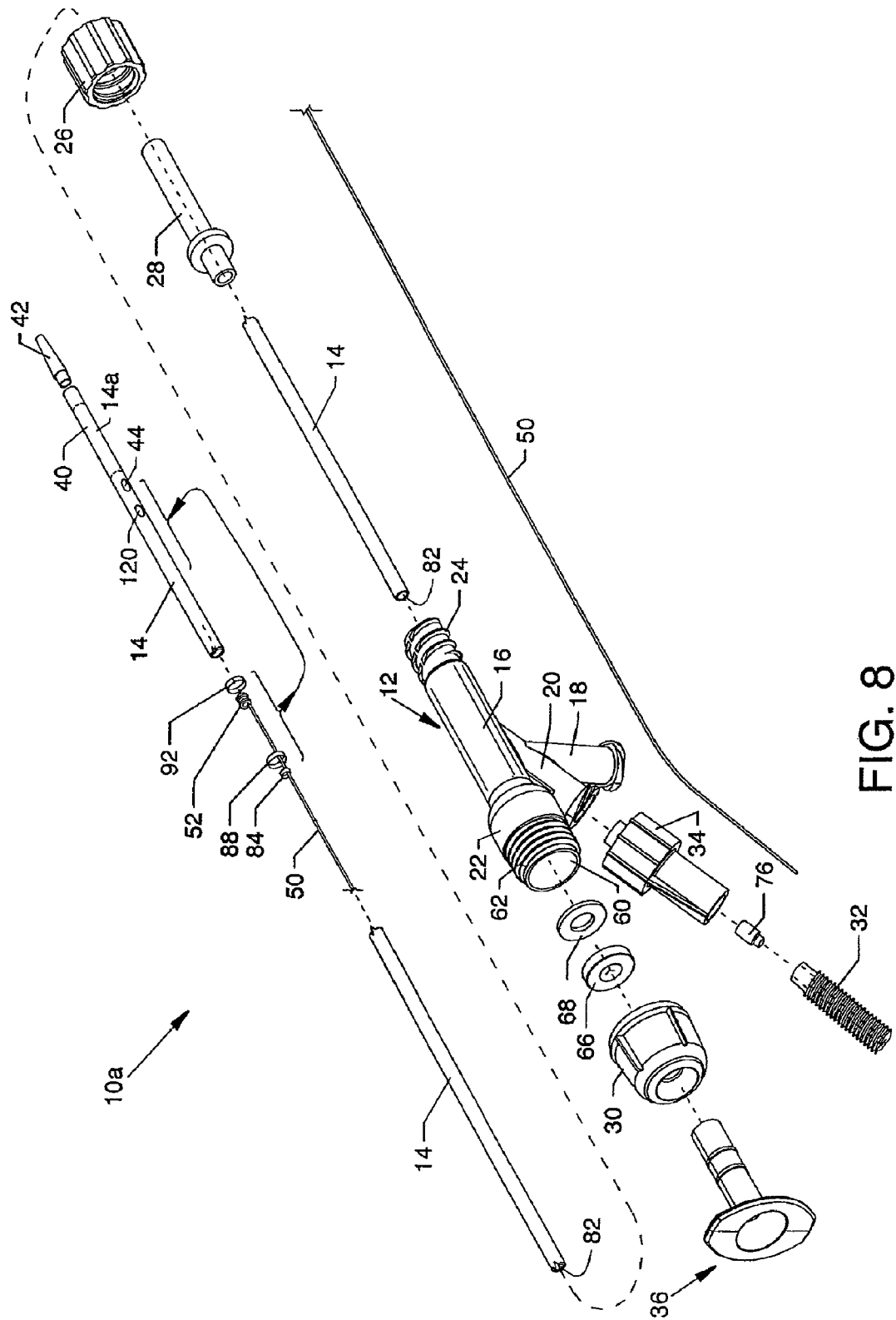
FIG. 8, a first alternative embodiment, is an illustration similar in many respects to FIG. 2 showing a rheolytic thrombectomy catheter having an inflow orifice in lieu of the inflow gap of the first embodiment.
Figure 9:
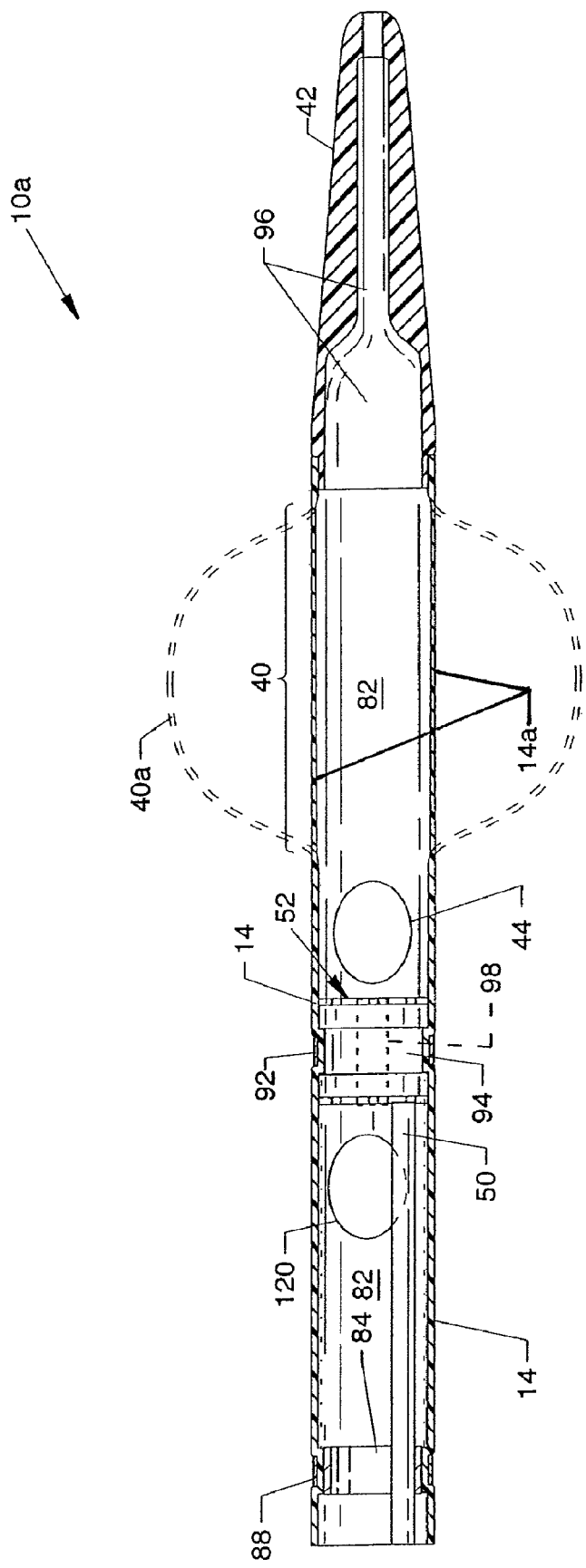
FIG. 9 is an illustration similar in many respects to FIG. 4 showing the distal end of the rheolytic thrombectomy catheter and the arrangement of a single inflow orifice in relation to the self-inflating balloon, to the fluid jet emanator, and to the balloon inflow inflation orifice.

FIG. 8, a first alternative embodiment, is an illustration similar in many respects to FIG. 2 showing a rheolytic thrombectomy catheter 10a having an inflow orifice 120 in lieu of inflow gap 38 of the first embodiment where all numerals correspond to those elements previously described or as otherwise described herein. In the alternative, more than one inflow orifice 120 could be utilized instead of the single inflow orifice 120. In this embodiment, catheter tube 14 is not interrupted by the use of inflow gap 38 and is characterized as having distal sections generally distal to fluid jet emanator 52 and proximal sections generally proximal to fluid jet emanator 52. FIG. 9 is an illustration similar in many respects to FIG. 4 showing the distal end of rheolytic thrombectomy catheter 10a and the arrangement of a single inflow orifice 120 in relation to self-inflating balloon 40, to fluid jet emanator 52 and to balloon inflow inflation orifice 44. In this embodiment, catheter tube 14 extends across the former location of inflow gap 38 of the first embodiment and is continuous thereacross. Fluid jet emanator 52 is secured in the manner previously described. The performance of the method and use thereof closely parallels that of the preferred embodiment of FIG. 1 by utilizing enabling connections to the ancillary devices shown in FIG. 6 whereby inflow orifice 120, instead of inflow gap 38, is used. High velocity fluid jet streams 103 of saline or other suitable fluids provide a low pressure region at inflow orifice 120 to ingest and entrain thrombotic particulate and/or debris 118.

Figure 10:
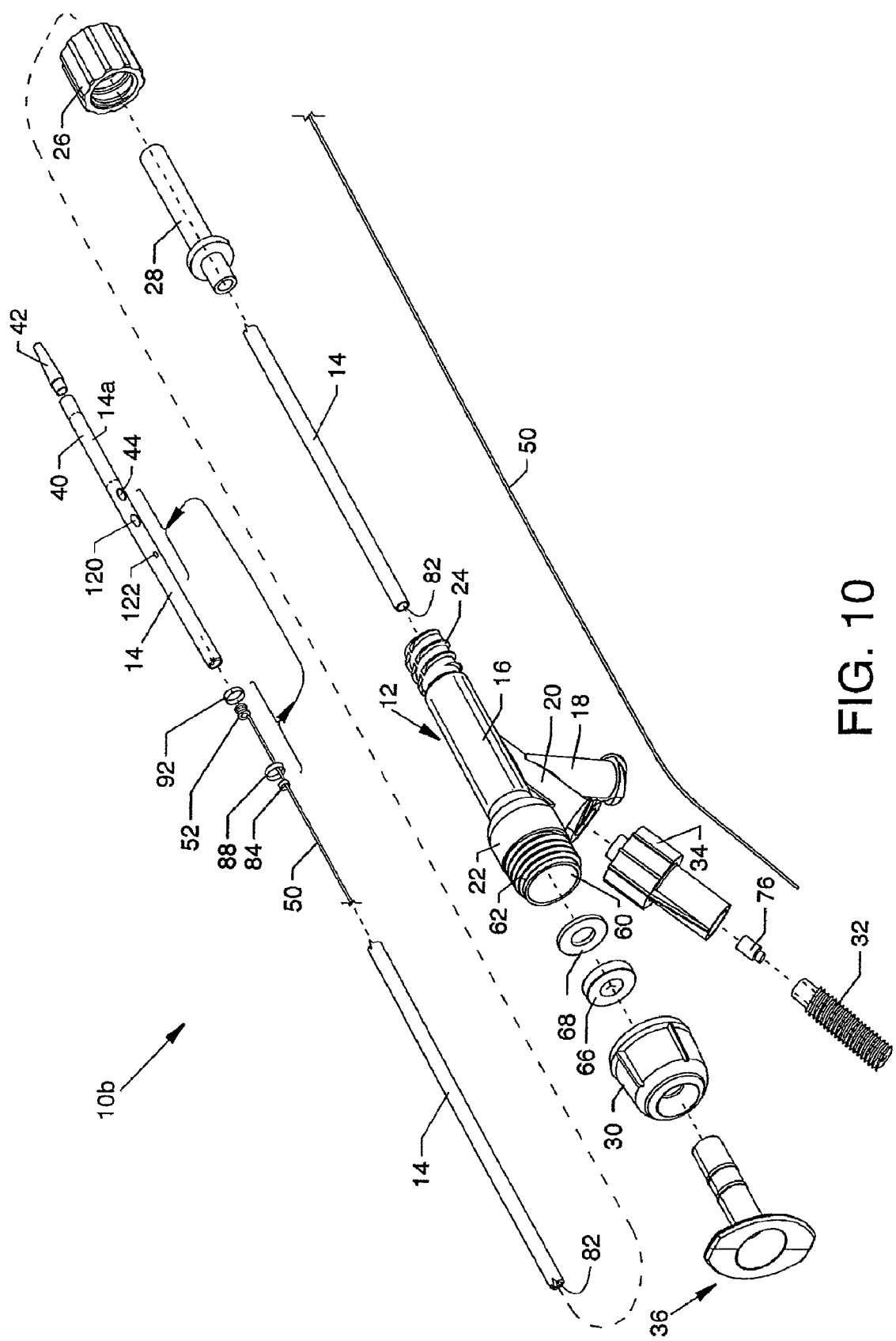
FIG. 10, a second alternative embodiment, is an illustration similar in many respects to FIG. 8 showing a rheolytic thrombectomy catheter.

FIG. 10, a second alternative embodiment, is an illustration similar in many respects to FIG. 8 showing a rheolytic thrombectomy catheter 10b, where all numerals correspond to those elements previously described or as otherwise described herein. An additional feature of rheolytic thrombectomy catheter 10b is an outflow orifice 122 located on the distal section of catheter tube 14 in a position proximal to inflow orifice 120. Optionally, the outflow orifice 122 is smaller than the inflow orifice as shown, for instance, in FIGS. 10 and 11.

Figure 11:
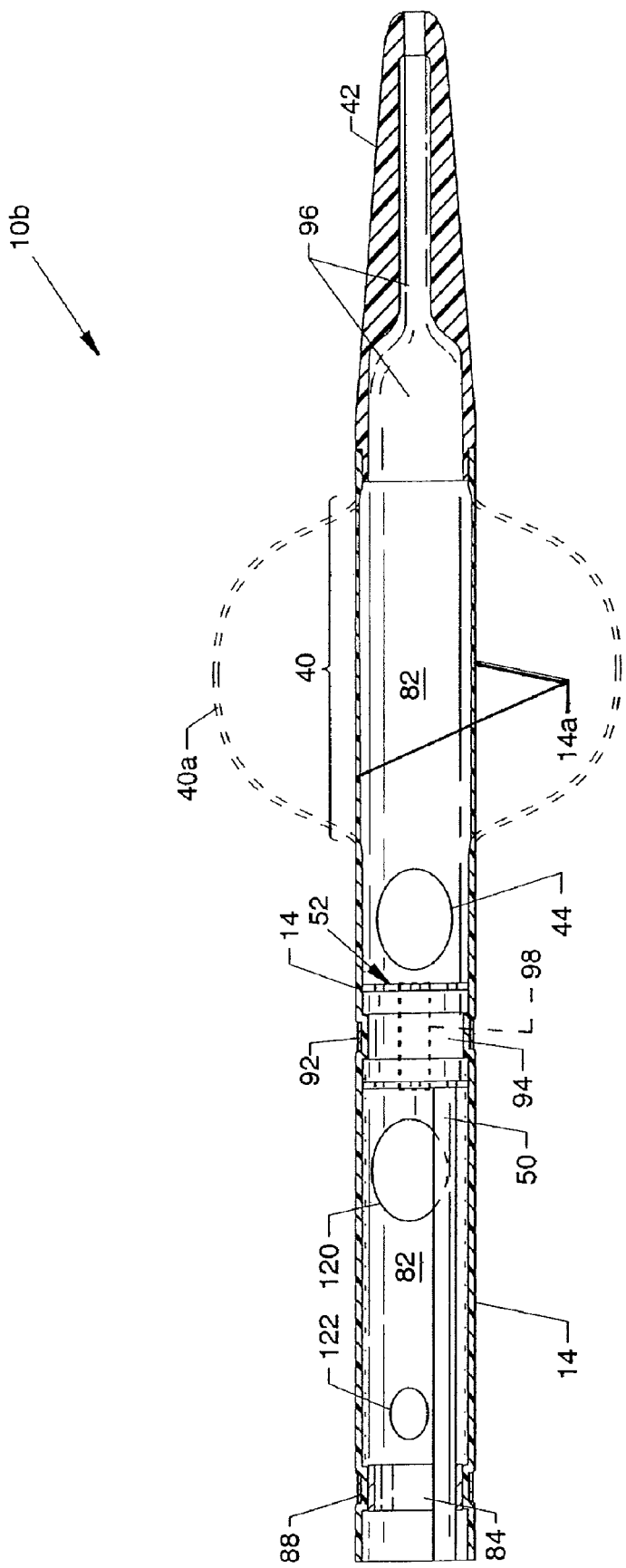
FIG. 11 is an illustration similar in many respects to FIG. 9 showing the distal end of the rheolytic thrombectomy catheter and the arrangement and relationship of the balloon inflation inflow orifice, the inflow orifice, the added outflow orifice, the fluid jet emanator, and the self-inflating balloon to each other.

FIG. 11 is an illustration similar in many respects to FIG. 9 showing the distal end of rheolytic thrombectomy catheter 10b and the arrangement and relationship of balloon inflation inflow orifice 44, inflow orifice(s) 120, added outflow orifice 122, fluid jet emanator 52, and self-inflating balloon 40 to each other. As with each of the embodiments disclosed herein, reduced wall thickness 14a of self-inflating balloon 40 can be formed from other materials, as known in the art, and then bonded or extruded to catheter tube 14 to maintain a continuous structure throughout the length of catheter tube 14.

Figure 12:
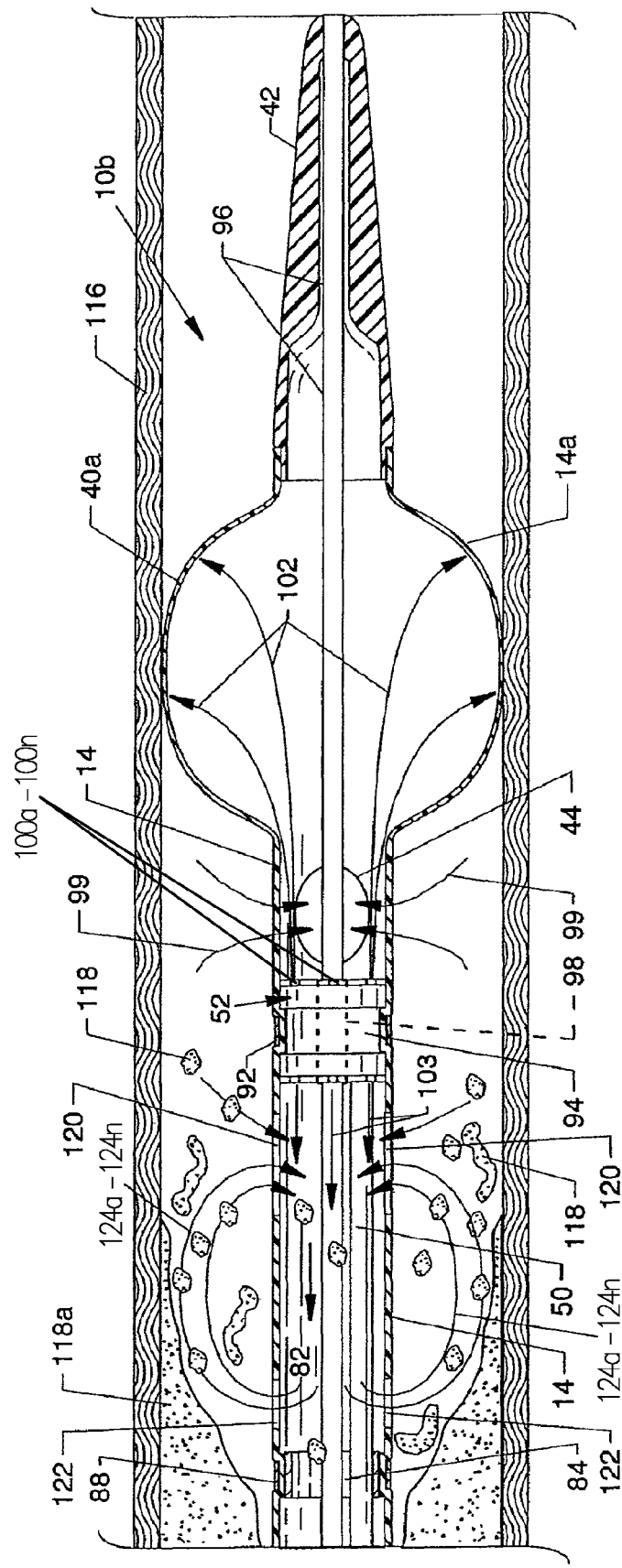
FIG. 12 is an illustration similar in many respects to FIG. 7 showing the operation of the rheolytic thrombectomy catheter in the performance of the method and use thereof.

FIG. 12 is an illustration similar in many respects to FIG. 7 showing the operation of rheolytic thrombectomy catheter 10b in the performance of the method and use thereof which closely parallels that of the preferred embodiment of FIG. 1 by utilizing enabling connections to the ancillary devices shown in FIG. 6. For purposes of example and illustration, balloon inflation inflow orifice 44 is oriented away from the viewer and one or more inflow orifices 120 and outflow orifices 122 are shown at the top and the bottom of catheter tube 14. Shown in particular is a cross section view of the distal and proximal sections of catheter tube 14 including inflated balloon 40a, flexible tapered tip 42, and other closely associated components positioned in a blood vessel 116, artery or the like at and having been positioned through the site of a thrombotic deposit or lesion 118a. As in previously described embodiments, the distal portion of high pressure tube 50 delivers a high pressure saline or other suitable fluid to fluid jet emanator 52 to produce and distribute high velocity fluid jet streams 102 of saline or other suitable fluids which are directed distally from orifices 100a-100n of fluid jet emanator 52 within and along the distal section of catheter tube 14 in close proximity to balloon inflation inflow orifice 44 and thence within the confines of self-inflating balloon 40 to cause the inflation of inflated balloon 40a for the purposes of, but not limited to, impeding fluid flow within blood vessel 116 to effect a stagnate flow in the thrombectomy region, to provide centering of the distal and proximal sections of catheter tube 14 and to accomplish thrombectomy functions as described herein. Subsequent to positioning of catheter tube 14, self-inflating balloon 40 is automatically and expandingly deployed to reform as an inflated balloon 40a primarily by the pressure of the pressurized distally directed high velocity fluid jet streams 102 of saline or other suitable fluid emanating from jet orifices 100a-100n of fluid jet emanator 52. Multiple high velocity fluid jet streams 103 of saline (or other suitable fluids) are emitted in a proximal direction from jet orifices 101a-101n of fluid jet emanator 52 and pass outwardly through one or more of outflow orifice(s) 122 in a radial direction. This action produces high velocity cross stream jet(s) 124a-124n directed outwardly toward the wall of blood vessel 116 and these jet(s) are influenced by the low pressure at inflow orifice(s) 120 to cause high velocity cross stream jet(s) 124 to flow distally and circumferentially to impinge on, provide drag forces on, and break up thrombotic deposits or lesions 118a. Then, by entrainment the jet(s) urge and carry along the loosened thrombotic particulate and/or debris 118 (and/or lesions) through the inflow orifice(s) 120, a relatively low pressure region, into the high velocity jet streams 103 where the thrombotic particulate and/or debris 118 (and/or lesions) is further macerated into microscopic particles, and thence into catheter tube lumen 82, and finally through lumen 82 for subsequent exhausting. The exhaust outflow is driven by an internal pressure which is created by high velocity fluid jet stream(s) 103 and the fluid entrained through inflow orifice(s) 120 to cause pressurization within lumen 82. An advantage provided by the distally located inflated balloon 40a is that in a no-flow situation where the distal flow of blood is stopped by inflation of intervening inflated balloon 40a, the particles of thrombotic particulate and/or debris 118 adjacent outflow orifice(s) 122 and inflow orifice(s) 120 are substantially trapped and can be more effectively circulated, recirculated and rediluted until all that remains is saline and minute particles of thrombotic particulate and/or debris 118. These particles are subsequently removed in a proximal direction through lumen 82 of catheter tube 14 by promoting flow via exhaust regulator 110. Another advantage is the utilization of the exhaust outflow and internal pressure which is created by high velocity fluid jet stream(s) 103 in combination with the restriction of the outflow, such as influenced by exhaust regulator 110, to cause automatic expansion of balloon 40 which forcibly impinges and seals against the inner wall of blood vessel 116. The reduced thickness of the material comprising balloon 40 allows balloon 40 to expand sufficiently to become an inflated balloon 40a which expansion is restricted by its impingement with the wall of blood vessel 116. Inflation pressure and fluid flows can be influenced by controlling the input fluid pressure at high pressure fluid pump 106 and by controlling the exhaust rate at exhaust regulator 110. Alternatively, other fluid jet emanators of different structures can be incorporated within the distal portion of catheter tube 14 as an alternative to jet emanator 52 to accomplish the same purpose as that described for fluid jet emanator 52.

Figure 13:
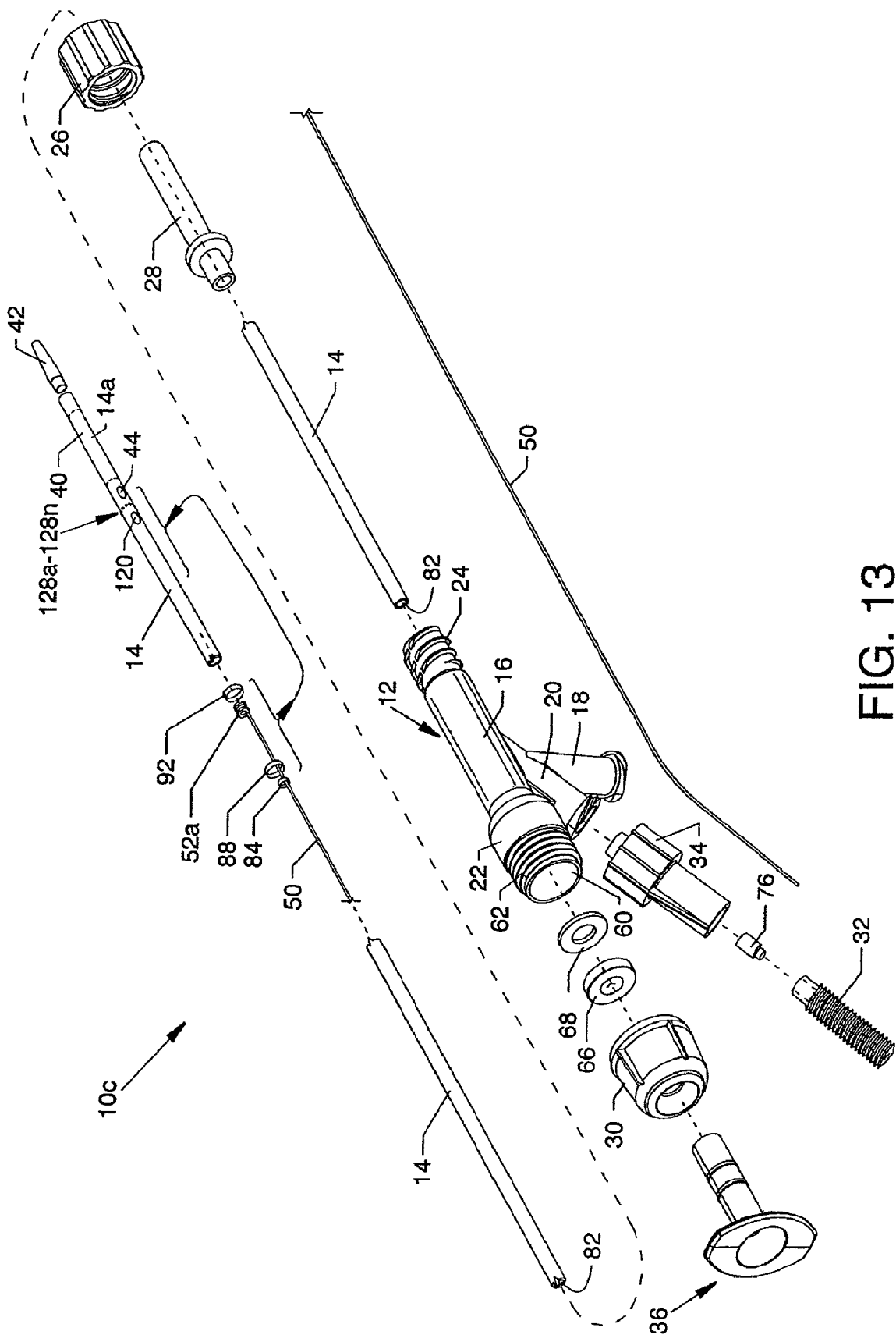
FIG. 13, a third alternative embodiment, is an illustration similar in many respects to FIG. 8 showing a rheolytic thrombectomy catheter.

FIG. 13, a third alternative embodiment, is an illustration similar in many respects to FIG. 8 showing a rheolytic thrombectomy catheter 10c, where all numerals correspond to those elements previously described or as otherwise described herein. An additional feature of rheolytic thrombectomy catheter 10c is a fluid jet emanator 52a corresponding in general design to that of fluid jet emanator 52 shown in FIG. 5, but including features which provide for the emanation of outwardly directed high velocity fluid radial jets 125a-125n therefrom, as shown in FIG. 14.

Figure 14:
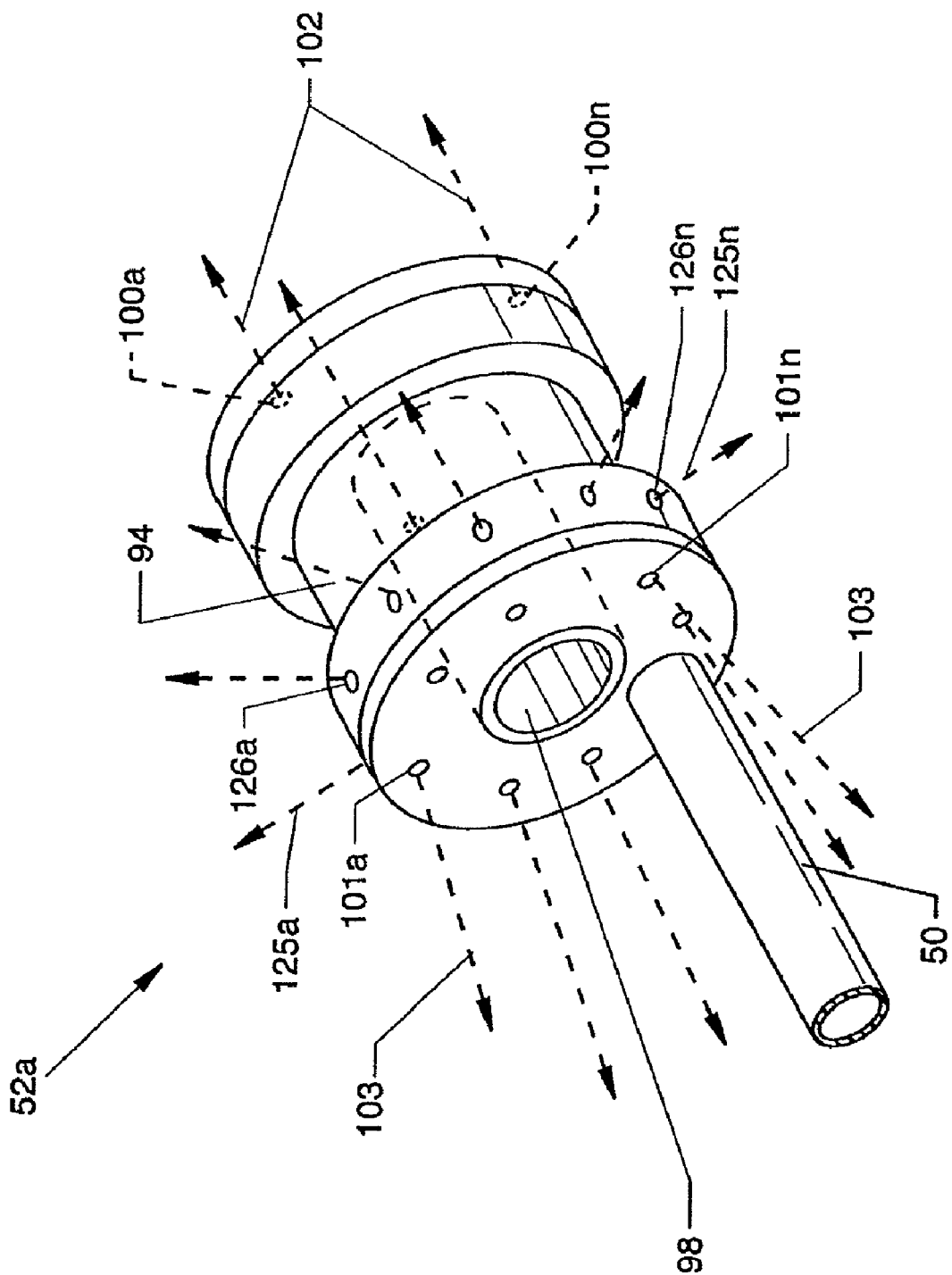
FIG. 14 is an illustration similar in many respects to FIG. 5 showing an alternative fluid jet emanator.

FIG. 14 is an illustration similar in many respects to FIG. 5 showing a fluid jet emanator 52a, where all numerals correspond to those elements previously described or as otherwise described herein. Additional uniformly aligned and spaced orifices 126a-126n, preferably in radial and perpendicular orientation with respect to the longitudinal axis, are arranged about the proximal peripheral circumference of fluid jet emanator 52a and are in communication with an internal manifold (not shown) and with jet orifices 101a-101n and provide for outwardly directed emanation of high velocity fluid radial jets 125a-125n of saline or other suitable fluids therefrom. In the alternative, the orientation of orifices 126a-126n can be randomly or otherwise angulated with respect to perpendicular orientation in order to provide high velocity fluid radial jets 125a-125n at other than perpendicular emanation therefrom and directed as desired.

Figure 15:
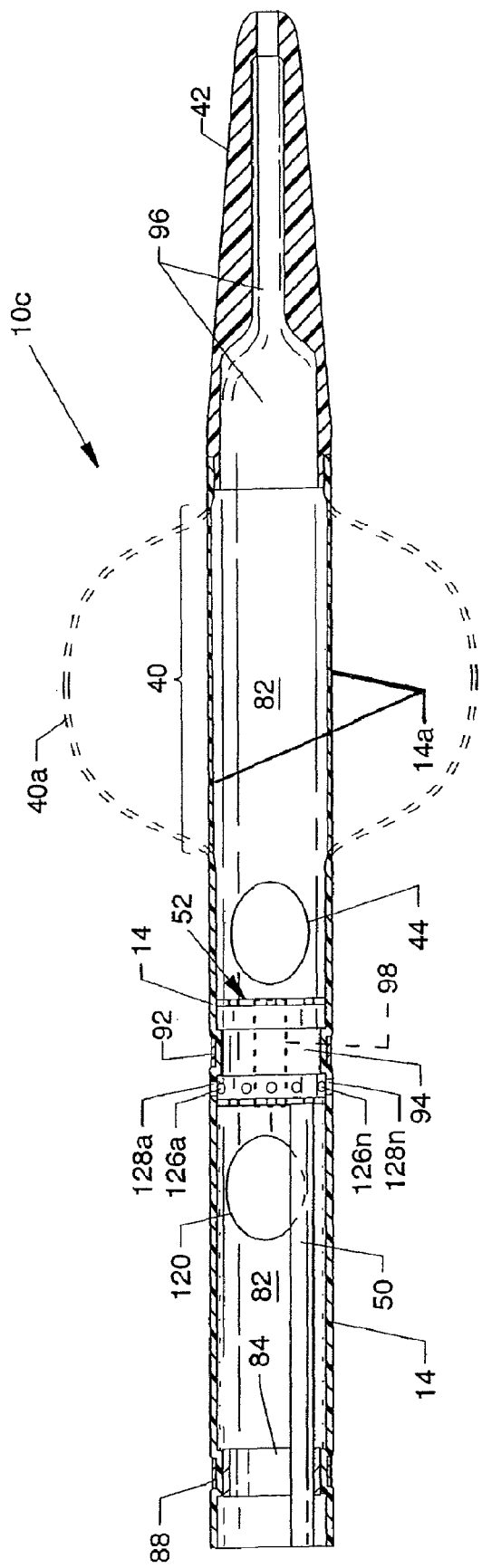
FIG. 15 is an illustration similar in many respects to FIG. 9 showing the distal end of the rheolytic thrombectomy catheter and the arrangement of the inflow orifice and the arrangement of the jet orifices of the fluid jet emanator and the arrangement of the balloon inflation inflow orifice in relation to the self-inflating balloon; and, FIG. 16 is an illustration closely related to FIGS. 7 and 12 showing the rheolytic thrombectomy catheter in the performance of the method and use thereof.

FIG. 15 is an illustration similar in many respects to FIG. 9 showing the distal end of rheolytic thrombectomy catheter 10c and the arrangement of inflow orifice 120 and the arrangement of jet orifices 126a-126n of fluid jet emanator 52a and the arrangement of balloon inflation inflow orifice 44 in relation to self-inflating balloon 40. Also shown is the plurality of holes 128a-128n extending through the wall of the catheter tube 14 in corresponding alignment with jet orifices 126a-126n. High velocity fluid radial jets 125a-125n (FIG. 14) emanate through jet orifices 126a-126n and through the plurality of holes 128a-128n in order to provide treatment, as shown and described in FIG. 16.

Figure 16:
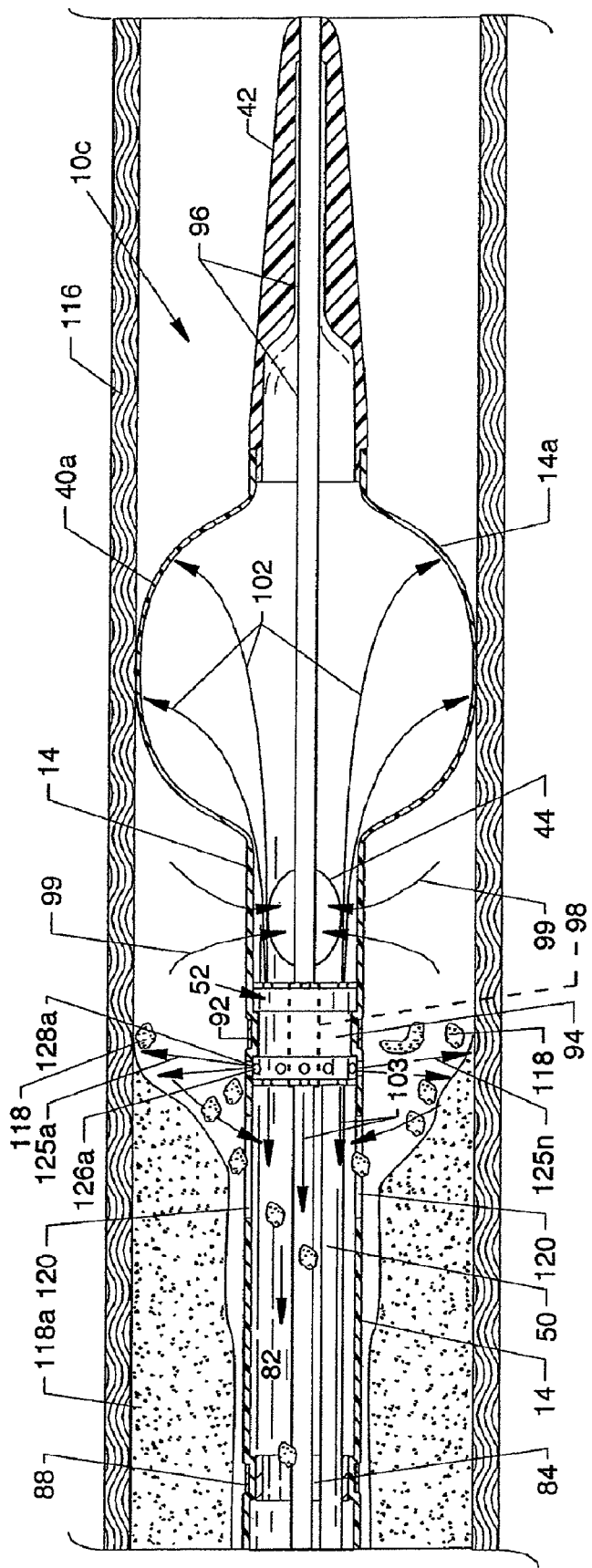

FIG. 16 is an illustration closely related to FIG. 7 and FIG. 12 showing rheolytic thrombectomy catheter 10b in the performance of the method and use thereof which closely parallels that of the preferred embodiment of FIG. 1 by utilizing enabling connections to the ancillary devices shown in FIG. 6. For purposes of example and illustration, balloon inflation inflow orifice 44 is oriented away from the viewer and one or more inflow orifices 120 are shown at the top and the bottom of catheter tube 14. The use of radially directed high velocity fluid radial jets 125a-125n from the radial jet orifices 126a-126n provides for impingement of thrombotic deposits or lesions 118a on the inner wall of blood vessel 116 adjacent to the region of inflow orifice(s) 120. This action impinges, ablates and loosens thrombotic deposits or lesions 118a, whereby thrombotic particulate and/or debris 118 (and/or lesions) and fluids can be then entrained by high velocity fluid jet streams 103 of saline or other suitable fluids and exhausted proximally through catheter tube 14. Additionally, drugs for treatment or for lysing of thrombotic deposits or lesions 118a can also be delivered via the radial jet orifices 126a-126n and high velocity fluid radial jets 125a-125n in order to soften the thrombotic deposits or lesions 118a in the region adjacent to the inflow orifice(s) 120, thereby benefiting and making use of high velocity fluid radial jets 125a-125n more effective. The drugs are delivered through high pressure tube 50 to the sites of the thrombotic deposits or lesions 118a using fluid jet emanator 52a, or could be delivered by the fluid jet emanators 52 and closely associated components in the previous embodiments.

Various modifications can be made to the device described in the present disclosure without departing from the apparent scope thereof.

It is claimed:

1. A thrombectomy catheter comprising:
a manifold having a central elongated tubular body with a proximal end and a distal end;
an elongated flexible catheter tube having a proximal end and a distal portion, said proximal end of said catheter tube extending into and distally from said distal end of said central elongated tubular body of said manifold;
said elongated flexible catheter tube continuous with an elongated distal section, said elongated distal section of said catheter tube having a proximal portion and a distal end;
a fluid jet emanator having a plurality of spaced jet orifices, said fluid jet emanator secured between the proximal portion of the elongated distal section and the distal portion of the elongated flexible catheter tube;
said elongated distal section having a first inflow orifice near said proximal portion thereof and distal relative to the secured fluid jet emanator;
said elongated flexible catheter tube having a second inflow orifice near said distal portion thereof and proximal relative to the secured fluid jet emanator;
a self-inflating balloon interposed between said first inflow orifice and said distal end of said elongated distal section; and
an elongated flexible high pressure tube having a proximal end in fluid communication with a fluid source and a distal end in fluid communication with the fluid jet emanator,
wherein the first inflow orifice is interposed between and in communication with the fluid jet emanator and the self-inflating balloon, and the self-inflating balloon is pressurized into an expanded configuration by a distal flow of fluid from the fluid jet emanator.

2. The thrombectomy catheter of claim 1, wherein said elongated flexible catheter tube has a predetermined wall thickness and said self-inflating balloon of said elongated distal section has a wall thickness less than said predetermined wall thickness.

3. The thrombectomy catheter of claim 1, wherein said elongated flexible catheter tube has a predetermined wall thickness and said self-inflating balloon is formed of a material with a wall thickness less than said predetermined wall thickness.

4. The thrombectomy catheter of claim 1, wherein the plurality of spaced jet orifices in said fluid jet emanator includes forwardly directed orifices and rearwardly directed orifices.

5. The thrombectomy catheter of claim 1, wherein said fluid source is selected from a group consisting of saline, a solution of one or more drugs and a combination of saline and a solution of one or more drugs.

6. The thrombectomy catheter of claim 1, wherein said self-inflating balloon has an approximate length between 2 mm and 200 mm.

7. The thrombectomy catheter of claim 1, wherein said self-inflating balloon has an approximate maximum inflated diameter between 2 mm and 20 mm at a pressure up to 20 ATM.

8. The thrombectomy catheter of claim 1, wherein said self-inflating balloon is pressurized into an expanded configuration by a distal flow of fluid from the fluid jet emanator and an entrained fluid from the first inflow orifice.

9. The thrombectomy catheter of claim 1, further comprising an outflow orifice that is smaller than both the first and second inflow orifices and is located proximal to the second inflow orifice.

10. A thrombectomy catheter comprising:
a manifold having a central elongated tubular body with a proximal end and a distal end;
an elongated flexible catheter tube having a proximal end and a distal portion, said proximal end of said catheter tube extending into and distally from said distal end of said central elongated tubular body of said manifold;
said elongated flexible catheter tube continuous with an elongated distal section, said elongated distal section of said catheter tube having a proximal portion and a distal end;
a fluid jet emanator having a plurality of spaced jet orifices, said fluid jet emanator secured between the proximal portion of the elongated distal section and the distal portion of the elongated flexible catheter tube;
said elongated distal section having a first inflow orifice near said proximal portion thereof and distal relative to the secured fluid jet emanator;
said elongated flexible catheter tube having a second inflow orifice near said distal portion thereof and proximal relative to the secured fluid jet emanator;
a self-inflating balloon interposed between said first inflow orifice and said distal end of said elongated distal section; and
an elongated flexible high pressure tube having a proximal end in fluid communication with a fluid source and a distal end in fluid communication with the fluid jet emanator,
wherein the first inflow orifice is interposed between and in communication with the fluid jet emanator and the self-inflating balloon, and the self-inflating balloon is pressurized into an expanded configuration by a distal flow of an entrained fluid from the first inflow orifice and the fluid jet emanator.

* * * * *